(12) United States Patent
Kalnin et al.

(10) Patent No.: US 9,381,237 B2
(45) Date of Patent: Jul. 5, 2016

(54) NEUTRALIZING IMMUNOGEN (NIMIV) OF RHINOVIRUS AND ITS USES FOR VACCINE APPLICATIONS

(71) Applicant: Sanofi Pasteur Biologics, LLC, Cambridge, MA (US)

(72) Inventors: Kirill Kalnin, Pelham, NH (US); Yanhua Yan, Westford, MA (US); Harold Kleanthous, Westford, MA (US)

(73) Assignee: Sanofi Pasteur Biologics, LLC, Cambridge, MA (US)

( * ) Notice: Subject to any disclaimer, the term of this patent is extended or adjusted under 35 U.S.C. 154(b) by 118 days.

(21) Appl. No.: 14/182,731

(22) Filed: Feb. 18, 2014

(65) Prior Publication Data

US 2014/0161833 A1 Jun. 12, 2014

Related U.S. Application Data

(62) Division of application No. 12/442,988, filed as application No. PCT/US2007/021053 on Oct. 1, 2007, now Pat. No. 8,652,486.

(60) Provisional application No. 60/848,451, filed on Sep. 29, 2006.

(51) Int. Cl.
| | |
|---|---|
| *A61K 39/125* | (2006.01) |
| *C07K 14/005* | (2006.01) |
| *C07K 16/10* | (2006.01) |
| *A61K 39/12* | (2006.01) |
| *A61K 39/00* | (2006.01) |

(52) U.S. Cl.
CPC .............. *A61K 39/125* (2013.01); *A61K 39/12* (2013.01); *C07K 14/005* (2013.01); *C07K 16/1009* (2013.01); *A61K 2039/525* (2013.01); *A61K 2039/55505* (2013.01); *A61K 2039/6081* (2013.01); *C12N 2770/32722* (2013.01); *C12N 2770/32734* (2013.01)

(58) Field of Classification Search
None
See application file for complete search history.

(56) References Cited

U.S. PATENT DOCUMENTS

| | | | |
|---|---|---|---|
| 5,541,100 | A | 7/1996 | Arnold et al. |
| 2003/0138769 | A1 | 7/2003 | Birkett |
| 2004/0146524 | A1 | 7/2004 | Lyons et al. |
| 2005/0272114 | A1 | 12/2005 | Darzins et al. |
| 2006/0067943 | A1* | 3/2006 | Maa .................. A61K 9/1652 424/184.1 |

FOREIGN PATENT DOCUMENTS

| | | |
|---|---|---|
| EP | 0169146 A2 | 1/1986 |
| WO | WO-2006/078648 A2 | 7/2006 |

OTHER PUBLICATIONS

Blaas et al., "Comparison of the three-dimensional structure of two human rhinoviruses (HRV2 and HRV14)," Proteins. 2(4):263-72 (1987).
Brown et al., "Foreign epitopes in immunodominant regions of hepatitis B core particles are highly immunogenic and conformationally restricted," Vaccine. 9(8):595-601 (1991).
Callahan et al., "Molecular cloning and complete sequence determination of RNA genome of human rhinovirus type 14," Proc Natl Acad Sci USA. 82(3):732-6 (1985).
Che et al., "Antibody-mediated neutralization of human rhinovirus 14 explored by means of cryoelectron microscopy and X-ray crystallography of virus-Fab complexes," J Virol. 72(6):4610-22 (1998).
Colonno et al., "Inhibition of rhinovirus attachment by neutralizing monoclonal antibodies and their Fab fragments," J Virol. 63(1):36-42 (1989).
Francis et al., "Immunological properties of hepatitis B core antigen fusion proteins," Proc Natl Acad Sci USA. 87(7):2545-9 (1990).
Laine et al., "Alignment of capsid protein VP1 sequences of all human rhinovirus prototype strains: conserved motifs and functional domains," J Gen Virol. 87(Pt. 1):129-38 (2006).
Laine et al., "Phylogenetic analysis of human rhinovirus capsid protein VP1 and 2A protease coding sequences confirms shared genus-like relationships with human enteroviruses," J Gen Virol. 86(Pt 3):697-706 (2005).
Ledford et al., "VP1 Capsid Protein [Human Rhinovirus 91]," NCBI, Mar. 15, 2004, <http://www.ncbi.nlm.nih.gov/protein/33469807>.
Ledford et al., "VP1 sequencing of all human rhinovirus serotypes: insights into genus phylogeny and susceptibility to antiviral capsid-binding compounds," J Virol. 78(7):3663-74 (2004).
Ledford et al., "VP1 Capsid Protein [Human Rhinovirus 5]," NCBI, Mar. 14, 2004, <http://www.ncbi.nlm.nih.gov/protein/33469635>.
McCray et al., "Different rhinovirus serotypes neutralized by antipeptide antibodies," Nature. 329(6141):736-8 (1987).
Patten et al., "Applications of DNA shuffling to pharmaceuticals and vaccines," Curr Opin Biotechnol. 8(6):724-33 (1997).
Palmenberg et al., "Polyprotein [Human Rhinovirus 52]," NCBI, Apr. 10, 2009, <http://www.ncbi.nlm.nih.gov/protein/217316507>.
Sherry et al., "Use of monoclonal antibodies to identify four neutralization immunogens on a common cold picornavirus, human rhinovirus 14," J Virol. 57(1):246-57 (1986).
Smith et al., "In search of dark horses: affinity maturation of phage-displayed ligands," Mol Divers. 2(1-2):2-4 (1996).
Extended European Search Report from European Patent Application No. 07867176.5, dated Mar. 25, 2010 (date of completion of search), and Apr. 21, 2010 (date of mailing of report).
Notice of Reasons for Rejection issued in Japanese Patent Application No. 2009-530456, dispatched Nov. 28, 2012 (English Language Translation Provided) (8 pages).
International Preliminary Report on Patentability from International Application No. PCT/US2007/021053 (WO 2008/057158), dated Jun. 3, 2009 (date of completion), and Jun. 19, 2009 (date of mailing of report).
International Search Report from International Application No. PCT/US2007/021053 (WO 2008/057158), dated May 6, 2008 (date of completion of search), and Jun. 3, 2008 (date of mailing of search report).
Written Opinion from International Application No. PCT/US2007/021053 (WO 2008/057158), dated May 7, 2008 (date of completion of opinion), and Jun. 3, 2008 (date of mailing of opinion).

\* cited by examiner

*Primary Examiner* — Stacy B Chen
(74) *Attorney, Agent, or Firm* — Clark & Elbing LLP; Susan M. Michaud

(57) ABSTRACT

The invention relates to methods and compositions for preventing or treating human rhinovirus infection.

24 Claims, 15 Drawing Sheets

Figure 7

NimIII Mabs neutralized CR6
~10 times less than HRV14

Figure 10

NimIV affects NimI, NimII, NimIII
50% neutralization titer

| mAbs / Viruses | Mab17 (αNimI) | Mab16 (αNimII) | Mab5 (αNimIII) |
|---|---|---|---|
| [virus 1] | 200 | ~60x10³ | ~1x10⁶ |
|  | 1.5X | 5X | 10X |
| [virus 2] | 300 | ~13x10³ | ~11x10⁶ |

Figure 14

50% neutralization titers of Nim-specific antibodies against CR6, CR72 and HRV14

|       | Mab4 (α-NimI) | Mab17 (α-NimII) | Mab16 (α-NimIII) | Mab5 (α-NimIII) |
|-------|---------------|-----------------|------------------|-----------------|
| CR72  | >1.0x10⁷      | ~200            | ND               | >1.0x10⁷        |
| CR6   | >1.0x10⁷      | ~200            | ~60x10³          | ~1x10⁶          |
| HRV14 | >1.0x10⁷      | ~300            | ~13

Figure 15

50% neutralization titers of anti-CR6 and anti-CR72 against HRV14, HRV6, HRV72, CR6 and CR72

| Virus | Serum | |
|---|---|---|
| | anti-CR6 | anti-CR72 |
| HRV14 | $6\times10^2$ | $2\times10^3$ |
| HRV6 | $6\times10^3$ | ND |
| HRV72 | ND | $5\times10^2$ |
| CR6 | $6\times10^3$ | ND |
| CR72 | ND | $2\times10^3$ |

SEQUENCE LISTING

```
<160> NUMBER OF SEQ ID NOS: 43

<210> SEQ ID NO 1
<211> LENGTH: 6
<212> TYPE: PRT
<213> ORGANISM: Rhinovirus (Human rhinovirus)

<400> SEQUENCE: 1

Pro Val Ile Lys Lys Arg
1               5

<210> SEQ ID NO 2
<211> LENGTH: 7
<212> TYPE: PRT
<213> ORGANISM: Rhinovirus (Human rhinovirus)

<400> SEQUENCE: 2

Pro Val Ile Lys Lys Arg Lys
1               5

<210> SEQ ID NO 3
<211> LENGTH: 7
<212> TYPE: PRT
<213> ORGANISM: Rhinovirus (Human rhinovirus)

<400> SEQUENCE: 3

Pro Val Ile Lys Lys Arg Glu
1               5

<210> SEQ ID NO 4
<211> LENGTH: 7
<212> TYPE: PRT
<213> ORGANISM: Rhinovirus (Human rhinovirus)

<400> SEQUENCE: 4

Pro Val Ile Lys Lys Arg Ser
1               5
```

```
<210> SEQ ID NO 5
<211> LENGTH: 7
<212> TYPE: PRT
<213> ORGANISM: Rhinovirus (Human rhinovirus)

<400> SEQUENCE: 5

Pro Val Ile Glu Lys Arg Thr
1               5

<210> SEQ ID NO 6
<211> LENGTH: 7
<212> TYPE: PRT
<213> ORGANISM: Rhinovirus (Human rhinovirus)

<400> SEQUENCE: 6

Pro Lys Ile Ile Lys Lys Arg
1               5

<210> SEQ ID NO 7
<211> LENGTH: 7
<212> TYPE: PRT
<213> ORGANISM: Rhinovirus (Human rhinovirus)

<400> SEQUENCE: 7

Pro Val Ile Lys Arg Arg Glu
1               5

<210> SEQ ID NO 8
<211> LENGTH: 7
<212> TYPE: PRT
<213> ORGANISM: Rhinovirus (Human rhinovirus)

<400> SEQUENCE: 8

Pro Ile Ile Ala Lys Arg Glu
1               5

<210> SEQ ID NO 9
<211> LENGTH: 7
<212> TYPE: PRT
<213> ORGANISM: Rhinovirus (Human rhinovirus)

<400> SEQUENCE: 9

Thr Ile Ile Lys Lys Arg Thr
1               5

<210> SEQ ID NO 10
<211> LENGTH: 16
<212> TYPE: PRT
<213> ORGANISM: Rhinovirus (Human rhinovirus)

<400> SEQUENCE: 10

Asn Thr Glu Pro Val Ile Lys Lys Arg Lys Gly Asp Ile Lys Ser Tyr
1               5                   10                  15

<210> SEQ ID NO 11
<211> LENGTH: 7
<212> TYPE: PRT
<213> ORGANISM: Rhinovirus (Human rhinovirus)

<400> SEQUENCE: 11

Thr Ile Val Lys Lys Arg Thr
1               5

<210> SEQ ID NO 12
```

```
<211> LENGTH: 7
<212> TYPE: PRT
<213> ORGANISM: Rhinovirus (Human rhinovirus)

<400> SEQUENCE: 12

Thr Ala Ile Val Thr Arg Pro
1               5

<210> SEQ ID NO 13
<211> LENGTH: 7
<212> TYPE: PRT
<213> ORGANISM: Rhinovirus (Human rhinovirus)

<400> SEQUENCE: 13

Val Ala Ile Arg Pro Arg Thr
1               5

<210> SEQ ID NO 14
<211> LENGTH: 7
<212> TYPE: PRT
<213> ORGANISM: Rhinovirus (Human rhinovirus)

<400> SEQUENCE: 14

Thr Ala Ile Val Arg Arg Asn
1               5

<210> SEQ ID NO 15
<211> LENGTH: 17
<212> TYPE: PRT
<213> ORGANISM: Rhinovirus (Human rhinovirus)

<400> SEQUENCE: 15

Cys Lys Asn Ile Val Pro Val Ile Lys Lys Arg Glu Asn Ile Thr Thr
1               5                   10                  15

Tyr

<210> SEQ ID NO 16
<211> LENGTH: 17
<212> TYPE: PRT
<213> ORGANISM: Rhinovirus (Human rhinovirus)

<400> SEQUENCE: 16

Cys Asn Thr Glu Pro Val Ile Lys Lys Arg Lys Gly Asp Ile Lys Ser
1               5                   10                  15

Tyr

<210> SEQ ID NO 17
<211> LENGTH: 17
<212> TYPE: PRT
<213> ORGANISM: Rhinovirus (Human rhinovirus)

<400> SEQUENCE: 17

Cys Asn Pro Lys Pro Val Ile Lys Lys Arg Glu Gly Asp Ile Lys Thr
1               5                   10                  15

Tyr

<210> SEQ ID NO 18
<211> LENGTH: 17
<212> TYPE: PRT
<213> ORGANISM: Rhinovirus (Human rhinovirus)

<400> SEQUENCE: 18

Lys Asn Lys Ile Val Pro Val Ile Lys Lys Arg Glu Asn Ile Thr Thr
```

<210> SEQ ID NO 19

<400> SEQUENCE: 19

000

<210> SEQ ID NO 20
<211> LENGTH: 16
<212> TYPE: PRT
<213> ORGANISM: Rhinovirus (Human rhinovirus)

<400> SEQUENCE: 20

Gln Ala Ile Val Pro Val Ile Lys Lys Arg Ser Leu Ile Thr Asn Tyr
1               5                   10                  15

<210> SEQ ID NO 21
<211> LENGTH: 15
<212> TYPE: PRT
<213> ORGANISM: Rhinovirus (Human rhinovirus)

<400> SEQUENCE: 21

Met Ile Thr Pro Val Ile Lys Lys Arg Asp Asn Ile Thr Thr Tyr
1               5                   10                  15

<210> SEQ ID NO 22
<211> LENGTH: 7
<212> TYPE: PRT
<213> ORGANISM: Rhinovirus (Human rhinovirus)

<400> SEQUENCE: 22

Thr Gln Gly Leu Lys Asn Ala
1               5

<210> SEQ ID NO 23
<211> LENGTH: 7
<212> TYPE: PRT
<213> ORGANISM: Rhinovirus (Human rhinovirus)

<400> SEQUENCE: 23

Thr Ala Asn Arg Gln Asn Asp
1               5

<210> SEQ ID NO 24
<211> LENGTH: 7
<212> TYPE: PRT
<213> ORGANISM: Rhinovirus (Human rhinovirus)

<400> SEQUENCE: 24

Thr Ala Asn Lys Gln Asn Gly
1               5

<210> SEQ ID NO 25
<211> LENGTH: 7
<212> TYPE: PRT
<213> ORGANISM: Rhinovirus (Human rhinovirus)

<400> SEQUENCE: 25

Gln Pro Asn Arg Gln Gly Glu
1               5

<210> SEQ ID NO 26

```
<211> LENGTH: 7
<212> TYPE: PRT
<213> ORGANISM: Rhinovirus (Human rhinovirus)

<400> SEQUENCE: 26

Ile Gln Gly Gln Lys Asn Glu
1               5

<210> SEQ ID NO 27
<211> LENGTH: 7
<212> TYPE: PRT
<213> ORGANISM: Rhinovirus (Human rhinovirus)

<400> SEQUENCE: 27

Asn Val Asn Lys Gln Asn Glu
1               5

<210> SEQ ID NO 28
<211> LENGTH: 7
<212> TYPE: PRT
<213> ORGANISM: Rhinovirus (Human rhinovirus)

<400> SEQUENCE: 28

Val Ala Asn Gln Gln Asn Glu
1               5

<210> SEQ ID NO 29
<211> LENGTH: 7
<212> TYPE: PRT
<213> ORGANISM: Rhinovirus (Human rhinovirus)

<400> SEQUENCE: 29

Thr Ala Asn Gln Gln Asn Thr
1               5

<210> SEQ ID NO 30
<211> LENGTH: 7
<212> TYPE: PRT
<213> ORGANISM: Rhinovirus (Human rhinovirus)

<400> SEQUENCE: 30

His Ala Asp Arg Gln Asn Glu
1               5

<210> SEQ ID NO 31
<211> LENGTH: 7
<212> TYPE: PRT
<213> ORGANISM: Rhinovirus (Human rhinovirus)

<400> SEQUENCE: 31

Asn Ala Asn Arg Gln Asn Glu
1               5

<210> SEQ ID NO 32
<211> LENGTH: 16
<212> TYPE: PRT
<213> ORGANISM: Rhinovirus (Human rhinovirus)

<400> SEQUENCE: 32

Asn Pro Lys Pro Val Ile Lys Lys Arg Glu Gly Asp Ile Lys Thr Tyr
1               5                   10                  15

<210> SEQ ID NO 33
<211> LENGTH: 16
<212> TYPE: PRT
```

<213> ORGANISM: Rhinovirus (Human rhinovirus)

<400> SEQUENCE: 33

Gln Asn Ile Lys Pro Val Ile Glu Lys Arg Thr Ser Ile Lys Gln Tyr
1               5                   10                  15

<210> SEQ ID NO 34
<211> LENGTH: 15
<212> TYPE: PRT
<213> ORGANISM: Rhinovirus (Human rhinovirus)

<400> SEQUENCE: 34

Asn Pro Pro Lys Ile Ile Lys Lys Arg Asp Thr Ile Asn Thr Tyr
1               5                   10                  15

<210> SEQ ID NO 35
<211> LENGTH: 15
<212> TYPE: PRT
<213> ORGANISM: Rhinovirus (Human rhinovirus)

<400> SEQUENCE: 35

Ser Ala Lys Pro Val Ile Lys Arg Arg Glu Gln Ile Thr Lys Tyr
1               5                   10                  15

<210> SEQ ID NO 36
<211> LENGTH: 15
<212> TYPE: PRT
<213> ORGANISM: Rhinovirus (Human rhinovirus)

<400> SEQUENCE: 36

Asp Ala Lys Pro Ile Ile Ala Lys Arg Glu Asn Ile Met Lys Tyr
1               5                   10                  15

<210> SEQ ID NO 37
<211> LENGTH: 15
<212> TYPE: PRT
<213> ORGANISM: Rhinovirus (Human rhinovirus)

<400> SEQUENCE: 37

Asp Ser Lys Thr Ile Ile Lys Lys Arg Thr Asn Ile Lys Thr Tyr
1               5                   10                  15

<210> SEQ ID NO 38
<211> LENGTH: 289
<212> TYPE: PRT
<213> ORGANISM: Rhinovirus (Human rhinovirus)

<400> SEQUENCE: 38

Gly Leu Gly Asp Glu Leu Glu Glu Val Ile Val Glu Lys Thr Lys Gln
1               5                   10                  15

Thr Val Ala Ser Ile Ser Ser Gly Pro Lys His Thr Gln Lys Val Pro
                20                  25                  30

Ile Leu Thr Ala Asn Glu Thr Gly Ala Thr Met Pro Val Leu Pro Ser
            35                  40                  45

Asp Ser Ile Glu Thr Arg Thr Thr Tyr Met His Phe Asn Gly Ser Glu
        50                  55                  60

Thr Asp Val Glu Cys Phe Leu Gly Arg Ala Ala Cys Val His Val Thr
65                  70                  75                  80

Glu Ile Gln Asn Lys Asp Ala Thr Gly Ile Asp Asn His Arg Glu Ala
                85                  90                  95

Lys Leu Phe Asn Asp Trp Lys Ile Asn Leu Ser Ser Leu Val Gln Leu
            100                 105                 110

```
Arg Lys Lys Leu Glu Leu Phe Thr Tyr Val Arg Phe Asp Ser Glu Tyr
        115                 120                 125

Thr Ile Leu Ala Thr Ala Ser Gln Pro Asp Ser Ala Asn Tyr Ser Ser
        130                 135                 140

Asn Leu Val Val Gln Ala Met Tyr Val Pro Pro Gly Ala Pro Asn Pro
145                 150                 155                 160

Lys Glu Trp Asp Asp Tyr Thr Trp Gln Ser Ala Ser Asn Pro Ser Val
                165                 170                 175

Phe Phe Lys Val Gly Asp Thr Ser Arg Phe Ser Val Pro Tyr Val Gly
                180                 185                 190

Leu Ala Ser Ala Tyr Asn Cys Phe Tyr Asp Gly Tyr Ser His Asp Asp
            195                 200                 205

Ala Glu Thr Gln Tyr Gly Ile Thr Val Leu Asn His Met Gly Ser Met
        210                 215                 220

Ala Phe Arg Ile Val Asn Glu His Asp Glu His Lys Thr Leu Val Lys
225                 230                 235                 240

Ile Arg Val Tyr His Arg Ala Lys His Val Glu Ala Trp Ile Pro Arg
                245                 250                 255

Ala Pro Arg Ala Leu Pro Tyr Thr Ser Ile Gly Arg Thr Asn Tyr Pro
            260                 265                 270

Lys Asn Thr Glu Pro Val Ile Lys Lys Arg Lys Gly Asp Ile Lys Ser
        275                 280                 285

Tyr

<210> SEQ ID NO 39
<211> LENGTH: 289
<212> TYPE: PRT
<213> ORGANISM: Rhinovirus (Human rhinovirus)

<400> SEQUENCE: 39

Gly Leu Gly Asp Glu Leu Glu Glu Val Ile Val Glu Lys Thr Lys Gln
1               5                   10                  15

Thr Val Ala Ser Ile Ser Ser Gly Pro Lys His Thr Gln Lys Val Pro
            20                  25                  30

Ile Leu Thr Ala Asn Glu Thr Gly Ala Thr Met Pro Val Leu Pro Ser
        35                  40                  45

Asp Ser Ile Glu Thr Arg Thr Thr Tyr Met His Phe Asn Gly Ser Glu
    50                  55                  60

Thr Asp Val Glu Cys Phe Leu Gly Arg Ala Ala Cys Val His Val Thr
65                  70                  75                  80

Glu Ile Gln Asn Lys Asp Ala Thr Gly Ile Asp Asn His Arg Glu Ala
                85                  90                  95

Lys Leu Phe Asn Asp Trp Lys Ile Asn Leu Ser Ser Leu Val Gln Leu
            100                 105                 110

Arg Lys Lys Leu Glu Leu Phe Thr Tyr Val Arg Phe Asp Ser Glu Tyr
        115                 120                 125

Thr Ile Leu Ala Thr Ala Ser Gln Pro Asp Ser Ala Asn Tyr Ser Ser
        130                 135                 140

Asn Leu Val Val Gln Ala Met Tyr Val Pro Pro Gly Ala Pro Asn Pro
145                 150                 155                 160

Val Glu Trp Asp Asp Tyr Thr Trp Gln Ser Ala Ser Asn Pro Ser Val
                165                 170                 175

Phe Phe Lys Val Gly Asp Thr Ser Arg Phe Ser Val Pro Tyr Val Gly
                180                 185                 190
```

Leu Ala Ser Ala Tyr Asn Cys Phe Tyr Asp Gly Tyr Ser His Asp Asp
                195                 200                 205

Glu Asp Thr Pro Tyr Gly Ile Thr Val Leu Asn His Met Gly Ser Met
    210                 215                 220

Ala Phe Arg Ile Val Asn Asp His Asp Ala His Arg Thr Leu Val Lys
225                 230                 235                 240

Ile Arg Val Tyr His Arg Ala Lys His Ile Glu Ala Trp Val Pro Arg
                245                 250                 255

Ala Pro Arg Ala Leu Pro Tyr Thr Ser Ile Gly Arg Thr Asn Tyr Pro
                260                 265                 270

Lys Asn Pro Lys Pro Val Ile Lys Lys Arg Gly Asp Ile Lys Thr
                275                 280                 285

Tyr

<210> SEQ ID NO 40
<211> LENGTH: 290
<212> TYPE: PRT
<213> ORGANISM: Rhinovirus (Human rhinovirus)

<400> SEQUENCE: 40

Gly Leu Gly Asp Glu Leu Glu Glu Val Ile Val Glu Lys Thr Lys Gln
1               5                   10                  15

Thr Val Ala Ser Ile Ser Ser Gly Pro Lys His Thr Gln Lys Val Pro
                20                  25                  30

Ile Leu Thr Ala Asn Glu Thr Gly Ala Thr Met Pro Val Leu Pro Ser
                35                  40                  45

Asp Ser Ile Glu Thr Arg Thr Thr Tyr Met His Phe Asn Gly Ser Glu
    50                  55                  60

Thr Asp Val Glu Cys Phe Leu Gly Arg Ala Ala Cys Val His Val Thr
65                  70                  75                  80

Glu Ile Gln Asn Lys Asp Ala Thr Gly Ile Asp Asn His Arg Glu Ala
                85                  90                  95

Lys Leu Phe Asn Asp Trp Lys Ile Asn Leu Ser Ser Leu Val Gln Leu
                100                 105                 110

Arg Lys Lys Leu Glu Leu Phe Thr Tyr Val Arg Phe Asp Ser Glu Tyr
            115                 120                 125

Thr Ile Leu Ala Thr Ala Ser Gln Pro Asp Ser Ala Asn Tyr Ser Ser
    130                 135                 140

Asn Leu Val Val Gln Ala Met Tyr Val Pro Pro Gly Ala Pro Asn Pro
145                 150                 155                 160

Val Glu Trp Asn Asp Tyr Thr Trp Gln Ser Ala Ser Asn Pro Ser Val
                165                 170                 175

Phe Phe Lys Val Gly Asp Thr Ala Arg Phe Ser Val Pro Phe Val Gly
                180                 185                 190

Leu Ala Ser Ala Tyr Asn Cys Phe Tyr Asp Gly Tyr Ser His Asp Asp
                195                 200                 205

Ala Glu Thr Gln Tyr Gly Ile Thr Val Leu Asn His Met Gly Ser Met
    210                 215                 220

Ala Phe Arg Ile Val Asn Glu His Asp Glu His Lys Thr Leu Val Lys
225                 230                 235                 240

Ile Arg Val Tyr His Arg Ala Lys His Val Glu Ala Trp Ile Pro Arg
                245                 250                 255

Ala Pro Arg Ala Leu Pro Tyr Thr Ser Ile Gly Arg Thr Asn Tyr Pro
                260                 265                 270

```
Lys Lys Asn Lys Ile Val Pro Val Ile Lys Lys Arg Glu Asn Ile Thr
        275                 280                 285

Thr Tyr
    290

<210> SEQ ID NO 41
<211> LENGTH: 27
<212> TYPE: PRT
<213> ORGANISM: Rhinovirus (Human rhinovirus)
<220> FEATURE:
<221> NAME/KEY: MISC_FEATURE
<222> LOCATION: (1)..(10)
<223> OTHER INFORMATION: Xaa = any amino acid or is absent
<220> FEATURE:
<221> NAME/KEY: MISC_FEATURE
<222> LOCATION: (11)..(11)
<223> OTHER INFORMATION: Xaa = Pro or Thr
<220> FEATURE:
<221> NAME/KEY: MISC_FEATURE
<222> LOCATION: (12)..(12)
<223> OTHER INFORMATION: Xaa = Val, Lys, or Ile
<220> FEATURE:
<221> NAME/KEY: MISC_FEATURE
<222> LOCATION: (14)..(14)
<223> OTHER INFORMATION: Xaa = Lys, Glu, Ile, or Ala
<220> FEATURE:
<221> NAME/KEY: MISC_FEATURE
<222> LOCATION: (15)..(15)
<223> OTHER INFORMATION: Xaa = Lys or Arg
<220> FEATURE:
<221> NAME/KEY: MISC_FEATURE
<222> LOCATION: (17)..(17)
<223> OTHER INFORMATION: Xaa = Ser, Glu, Asp, Thr, Arg, or Lys
<220> FEATURE:
<221> NAME/KEY: MISC_FEATURE
<222> LOCATION: (18)..(27)
<223> OTHER INFORMATION: Xaa = any amino acid or is absent

<400> SEQUENCE: 41

Xaa Xaa Xaa Xaa Xaa Xaa Xaa Xaa Xaa Xaa Xaa Xaa Ile Xaa Xaa Arg
1               5                   10                  15

Xaa Xaa Xaa Xaa Xaa Xaa Xaa Xaa Xaa Xaa Xaa
            20                  25

<210> SEQ ID NO 42
<211> LENGTH: 6
<212> TYPE: PRT
<213> ORGANISM: Rhinovirus (Human rhinovirus)
<220> FEATURE:
<221> NAME/KEY: MISC_FEATURE
<222> LOCATION: (1)..(1)
<223> OTHER INFORMATION: Xaa = Asp or Glu

<400> SEQUENCE: 42

Xaa Asn Ile Thr Thr Tyr
1               5

<210> SEQ ID NO 43
<211> LENGTH: 6
<212> TYPE: PRT
<213> ORGANISM: Rhinovirus (Human rhinovirus)

<400> SEQUENCE: 43

Ser Leu Ile Thr Asn Tyr
1               5
```

NEUTRALIZING IMMUNOGEN (NIMIV) OF RHINOVIRUS AND ITS USES FOR VACCINE APPLICATIONS

FIELD OF THE INVENTION

The invention relates to methods and compositions for preventing or treating human rhinovirus infection.

BACKGROUND OF THE INVENTION

Human rhinoviruses (HRVs) represent the single most important etiological agents of the common cold (Arruda et al., *J. Clin. Microbiol.* 35:2864-2868 (1997); Couch, "Rhinoviruses." In: Fields, B. N., Knipe, D. M. (Eds.), *Virology*. Raven Press, New York, 607-629 (1990); Turner, *Antivir. Res.* 49(1):1-14 (2001)). HRVs causing about one-third of the outbreaks of the common cold are represented by about 100 serotypes, the convalescent sera from patients infected with which are not fully cross-neutralizing. Although HRV-induced upper respiratory illness is often mild and self-limiting, the socioeconomic impact caused by missed work or school is enormous and the degree of inappropriate antibiotic use is significant. It has been estimated that upper respiratory disease accounts for at least 25 million absences from work and 23 million absences of school annually in the United States (Anzueto et al., *Chest* 123(5):1664-1672 (2003); Rotbart, *Antivir. Res.* 53:83-98 (2002)).

There is increasing evidence of a link between HRV infection and more serious medical complications. For example, HRV-induced colds are the important predisposing factors to acute otitis media and sinusitis, and are major factors in the induction of exacerbations of asthma in adults and children. HRV infections are also associated with lower respiratory tract syndromes in individuals with cystic fibrosis, bronchitis, and other underlying respiratory disorders (Gern, *Pediatr. Infect. Dis. J.* 23:S78-S86 (2004); Anzueto et al., *Chest* 123 (5):1664-1672 (2003); Gem et al., *Clin. Microbiol. Rev.* 12(1):9-18 (1999); Pitkaranta et al., *J. Clin. Microbiol.* 35:1791-1793 (1997); Pitkaranta et al., *Pediatrics* 102:291-295 (1998); Rotbart, *Antivir. Res.* 53:83-98 (2002)).

To date, no effective antiviral therapies have been approved for either the prevention or treatment of diseases caused by HRV infection. Thus, there exists a significant unmet medical need to find agents that can prevent HRV infection, shorten the duration of HRV-induced illness, lessen the severity of symptoms, minimize secondary bacterial infections and exacerbations of underlying disease, and reduce virus transmission. A prophylactic HRV vaccine should be protective against a wide variety of serotypes to reduce the number of HRV infections and their clinical impact.

Attempts to make HRV vaccines based on synthetic peptides corresponding to conserved regions of structural proteins alone (McCray et al., *Nature* 329:736-738 (1987)) or as a part of biological fusions (Brown et al., *Vaccine* 9:595-601 (1991); Francis et al., *Proc. Natl. Acad. Sci. U.S.A.* 87:2545-2549 (1990)) have had limited success, due to low immunogenicity of chosen peptides, which may be partially explained by their low exposure on the virus surface (limited access to antibodies) or conformational constraints.

The present invention overcomes these limitations and features a vaccine that elicits a protective serotype cross-reactive neutralizing antibody response to prevent and treat HRV infection.

SUMMARY OF THE INVENTION

The invention provides isolated rhinovirus neutralizing immunogen IV (NimIV) peptides. These peptides can be from any serotype of rhinovirus, such as human rhinoviruses (e.g., HRV14). The peptides can include, for example, amino acids 277-283 (e.g., amino acids 275-285) of the carboxyl terminal region of virus structural protein 1 (VP 1) of a human rhinovirus. Exemplary sequences include the following: PVIKKR, PVIKKRK (HRV14), PVIKKRE (HRV6 and HRV72), PVIKKRS(HRV92), PVIEKRT (HRV83), PKIIKKR (HRV86), PVIKRRE (HRV35), PIIAKRE (HRV79), TIIKKRT (HRV3), NTEPVIKKRKGDIKSY (HRV14), and A-$X_1$-$X_2$-I-$X_3$-$X_4$-R-$X_5$-B, where $X_1$=P or T; $X_2$=V, K, or I; $X_3$=K, E, I, or A; $X_4$=K or R; $X_5$=S, E, D, T, R, T, or K; A=0-10 additional amino acids; and B=0-10 additional amino acids.

The invention also includes isolated nucleic acid molecules encoding a NimIV peptides or complements thereof. Further, the invention includes vectors (e.g., HRV14 vectors) including the peptides and nucleic acid molecules of the invention. The vectors can be, for example, human rhinovirus vectors, e.g., human rhinovirus vectors of a serotype different from that of the human rhinovirus from which the NimIV peptide is derived. In one example, the NimIV peptide or nucleic acid molecule is present in said human rhinovirus vector in place of NimIV sequences originally present in said vector. In other examples, the human rhinovirus from which the NimIV peptide is derived is human rhinovirus 6 (HRV6) or human rhinovirus 72 (HRV72). The latter peptides may be included in, e.g., a human rhinovirus 14 (HRV14) vector. In other examples, the VP1 protein or nucleic acid molecule of the vector is replaced with the VP1 protein or nucleic acid of the human rhinovirus from which the NimIV peptide is derived. In additional examples, the vector includes an inactivated human rhinovirus, to which the NimIV peptide is cross-linked, or a hepatitis B core sequence to which NimIV sequences are fused (see, e.g., Fiers et al., *Virus Res.* 103:173-176, 2004; WO 2005/055957; US 2003/0138769 A1; US 2004/0146524A1; US 2007/0036826 A1).

The invention further includes pharmaceutical compositions including the peptides, nucleic acid molecules, and vectors described herein. Optionally, the pharmaceutical compositions also include one or more of a pharmaceutically acceptable diluents, excipients, carriers, and/or adjuvants. Exemplary adjuvants include chitin microparticles and aluminum compounds. Further, the compositions can optionally include one or more additional human rhinovirus neutralizing immunogens.

Also included in the invention are methods of inducing an immune response to a rhinovirus in a subject. These methods involve administering to the subject an isolated NimIV peptide or nucleic acid molecule. In some examples, the subjects does not have but is at risk of developing rhinovirus infection. In other examples, the subject has rhinovirus infection.

Definitions

By "administration" or "administering" is meant a method of giving a dosage of a composition of the invention to a mammal (e.g., a human), where the method is, e.g., intranasal, topical, systemic, inhalation, oral, intravenous, sub-cutaneous, intravascular, intra-arterial, intratumor, intraperitoneal, intraventricular, intraepidural, nasal, rectal intrascleral, ophthalmic, intraocular, or intramuscular. The preferred method of administration can vary depending on various factors, e.g., the components of the pharmaceutical composition, site of the potential or actual disease (e.g., the location of a tumor or vascular condition to be treated) and the severity of disease.

By "human rhinovirus" (HRV) is meant any member of the family Picornaviridae genus *Rhinovirus*. HRV can be classified by serotype, of which approximately 100 are known to exist. For example, HRV14, HRV6, HRV37, and HRV92 refer to human rhinoviruses of serotypes number 14, 6, 37, and 92 respectively.

By "pharmaceutically acceptable carrier" is meant a carrier that is physiologically acceptable to a treated mammal, while retaining the prophylactic or therapeutic properties of the compound with which it is administered. One exemplary pharmaceutically acceptable carrier is physiological saline. Other physiologically acceptable carriers and their formulations are known to those skilled in the art and examples are described, for example, in *Remington's Pharmaceutical Sciences*, ($18^{th}$ edition), ed. A. Gennaro, 1990, Mack Publishing Company, Easton, Pa. incorporated herein by reference.

By "neutralizing immunogen" (Nim) is meant a human rhinovirus (HRV) sequence that, upon introduction into a human, elicits anti-HRV neutralizing antibodies. In the case of recombinant HRV vaccines as described herein, the NimIV serotype is placed in superscript to specifically describe the source of the Nim (e.g., $\text{NimIV}^{HRV6}$ refers to a NimIV sequence derived from the HRV6 serotype).

A "neutralizing immunogen IV peptide" or "NimIV peptide" is a peptide having a sequence from the carboxyl terminal region (e.g., amino acids 274-289, using HRV14 (NTEPVIKKRKGDIKSY) as a reference; see FIG. 12B) of a rhinovirus virus structural protein 1 (VP1). NimIV peptides can include the specified sequences, additional flanking sequences, or only a core, conserved sequence, as described below. In addition, the peptides may be unmodified, and thus be identical to naturally occurring NimIV sequences, or may include one or more substitutions, deletions, insertions, or other modifications (e.g., 1, 2, 3, 4, 5, 6, 7, 8, 9, 10, 11, 12, 13, 14, 15, 16, 17, 18, 19, 20, 21, 22, 23, 24, or 25 substitutions, deletions, or insertions), provided that immunogenicity of the peptide is substantially maintained. Further, the NimIV peptides may comprise L or D amino acids, or mixtures thereof.

Examples of NimIV peptide sequences that can be used in the invention are listed below. The peptides can be, for example, 5-30, 8-25, 10-20, 14-19, 15-18, or 16-17 amino acids in length. The peptides may include a core NimIV sequence and, optionally, be flanked with additional NimIV sequences or linker sequences (e.g., 1, 2, 3, 4, 5, 6, 7, 8, 9, or 10 amino acids on amino and/or carboxyl terminal ends).

Examples of core NimIV sequences include PVIKKR, PVIKKRK (HRV14), PVIKKRE (HRV6 and HRV72), PVIKKRS (HRV92), PVIEKRT (HRV83), PKIIKKR (HRV86), PVIKKRE (HRV35), PIIAKRE (HRV79), TIIKKRT (HRV3), TIVKKRT (HRV3), TAIVTRP (HRV2), VAIRPRT (HRV16), TAIVRRN (HRV1A), NTEPVIKKRKGDIKSY (HRV14), as well as other HRV sequences that align with these sequences (see, for example, FIG. 11). The core sequence may be defined, for example, by the formula $A\text{-}X_1\text{-}X_2\text{-}I\text{-}X_3\text{-}X_4\text{-}R\text{-}X_5\text{-}B$, where $X_1$=P or T; $X_2$=V, K, or I; $X_3$=K, E, I, or A; $X_4$=K or R; $X_5$=S, E, D, T, R, T, or K; A=0-10 additional amino acids; and B=0-10 additional amino acids. The sequence of A and/or B can be naturally occurring NimIV/VP1 sequences, artificial sequences (e.g., linker sequences), or mixtures thereof.

A "neutralizing immunogen IV nucleic acid molecule" or "NimIV nucleic acid molecule" is a nucleic acid molecule encoding a NimIV peptide as defined herein or the complement thereof.

A NimIV peptide or nucleic acid molecule is "isolated" if it does not include flanking sequences with which it is contiguous in naturally occurring virus. Such peptides or nucleic acid molecules may be limited by, for example, the full-length sequence of VP1, the carboxyl terminal half of VP1, the carboxyl terminal quarter of VP1, or the carboxyl terminal 15-30 amino acids of VP1, or corresponding regions of nucleic acid sequences (see, e.g., Laine et al., *J. Gen. Virol.* 87:129-138, 2006).

A NimIV peptide "consists essentially of" a specified sequence, if it includes only that sequence, as well as possibly a minimal amount of flanking sequences (e.g., 1-10, 2-9, 3-8, 4-7, or 5-6 amino acids), on amino and/or carboxyl terminal ends, which may be naturally occurring sequences, artificial sequences (e.g., linkers), or combinations thereof. Such sequences can be present in the context of larger sequences (e.g., heterologous virus or other vector sequences).

A NimIV nucleic acid molecule "consists essentially of" a specified sequence, if it includes only that sequence, as well as possibly minimal amount of flanking sequences (e.g., 3-30, 6-27, 9-24, 12-21, or 15-18 nucleotides), on 5' and/or 3' ends, which may be naturally occurring sequences; artificial sequences (e.g., linkers), or combinations thereof. Such sequences can be present in the context of larger sequences (e.g., heterologous virus or other vector sequences).

Other features and advantages of the invention will be apparent from the following Detailed Description, the Drawings, and the Claims.

BRIEF DESCRIPTION OF THE DRAWINGS

FIG. 1 is a diagram of the structural region of CR6 genome (lower panel) and amino acid alignment of NimIV sequences of HRV6 (SEQ ID NO: 18) and HRV14 (SEQ ID NO: 10) (upper panel).

FIGS. 2A and 2B are graphs showing the results of plaque reduction neutralization assays of CR6 (a chimera including HRV14 sequences, with the exception of NimIV sequences, which are HRV6 sequences; also referred to herein as CR6; the right-hand bar of each pair (green)) and HRV14 (the left-hand bar of each pair (brown)) with guinea pig polyclonal antibodies anti-HRV14 (FIG. 2A) and anti-HRV6 (FIG. 2B). 20K, 40K, 60K, 80K correspond to titers of antibodies $2\times10^4$, $4\times10^4$, $6\times10^4$, and $8\times10^4$ respectively. The upper (green) and lower (brown) dashed lines indicate 50% reduction of plaque number for HRV14 and HRV6, respectively.

FIGS. 3A-3D are three-dimensional models of HRV14 and CR6. FIGS. 3A and 3B are 3D models of an HRV14 virus particle designed on the basis of known crystal structure (Che et al., *J. Virol.* 72:4610-4622 (1998)) using Chimera software (http://www.cgl.ucsf.edu/chimera/). VP1, Vp2, and VP2 are shown in dark blue, magenta, and grey colors, respectively. The HRV14 particle is presented as spacefill model, where Nims are color-coded onto its Van-der-Vaals surface. Green, blue, and magenta wired surfaces depict NimIII, NimIV, and NimII, respectively. Contact of NimIV with NimIII is shown to be provided through K287. Note that NimI on this model is covered by NimI-specific Fab17 shown by dark green.

FIGS. 3C and 3D are 3D models prepared using Accelrys Discovery Studio v1.5.1 (Accelrys Software, Inc.). FIG. 3C—Spacefill model of NimI, NimII, NimIII, and NimIV of HRV14 particle. Amino acid residues of Nims are depicted by Van Der Vaals solid surfaces. Positively and negatively charged surfaces are shown in blue and red, respectively. FIG. 3D—Comparison of spacefill models of HRV14 and CR6 viruses (NimIII and NimIV are only shown). The structure of CR6 was predicted on the basis of known crystal structure (see above) and information on protein sequence CR6 (see FIG. 1). Note: close contact of positively charged K287 from NimIV of HRV14 with negative residues of NimIII, whereas in CR6 due to K287T substitution this connection is abrogated.

FIG. 4 shows the results of neutralization of CR6 with mouse anti-HRV37, anti-HRV92, and anti-HRV6 sera. FIG. 4A is an alignment of NimIV for HRV14 (SEQ ID NO: 10), HRV37 (SEQ ID NO: 21), HRV6 (SEQ ID NO: 18), and HRV92 (SEQ ID NO: 20). Amino acids are numbered (below) according to an HRV14 template. Identical regions are shown in the rectangles (blue). FIG. 4B is a series of graphs showing the results of plaque reduction neutralization test (PRNT) studies of HRV14 (the left-hand bar of each pair; brown) and CR6 (the right-had bar of each pair; green) with anti-HRV37, anti-HRV92, and anti-HRV6 mouse antibodies generated against corresponding purified viruses. 50% neutralization titers are shown by either dashed lines on the graphs or numerically (50% NUT) in the boxed panel of the picture beneath correspondent graphs.

FIG. 5 shows experimental data based on NimIV$^{HRV6}$- and NimIV$^{HRV14}$-specific synthetic peptides. FIG. 5A is a Western blot of KLH-linked peptides H6 (NimIV$^{HRV6}$) and H14 (NimIV$^{HRV14}$) detected by guinea pig anti-HRV14 (GP14) and anti-HRV6 (GP6) polyclonal antibodies. FIG. 5B is a Western blot of free H6 and H14 peptides detected with the same antibodies; lane (1)—protein weight marker, lane (2)—H6-KLH (A) or H6 (B), lane (3)—H14-KLH (A) or H14 (B). FIG. 5C is a graph showing the results of ELISA analysis of H6 and H14 with GP6 and GP14.

FIG. 7 is a graph showing the results of plaque reduction neutralization test (PRNT) studies of HRV14 and CR6, which shows that a NimIII monoclonal antibody (Mab5)) neutralized CR6 about ten fold less than HRV14.

FIG. 10 is a table showing that NimIV affects NimI, NimII, and NimIII (50% neutralization titer).

Figure 13:
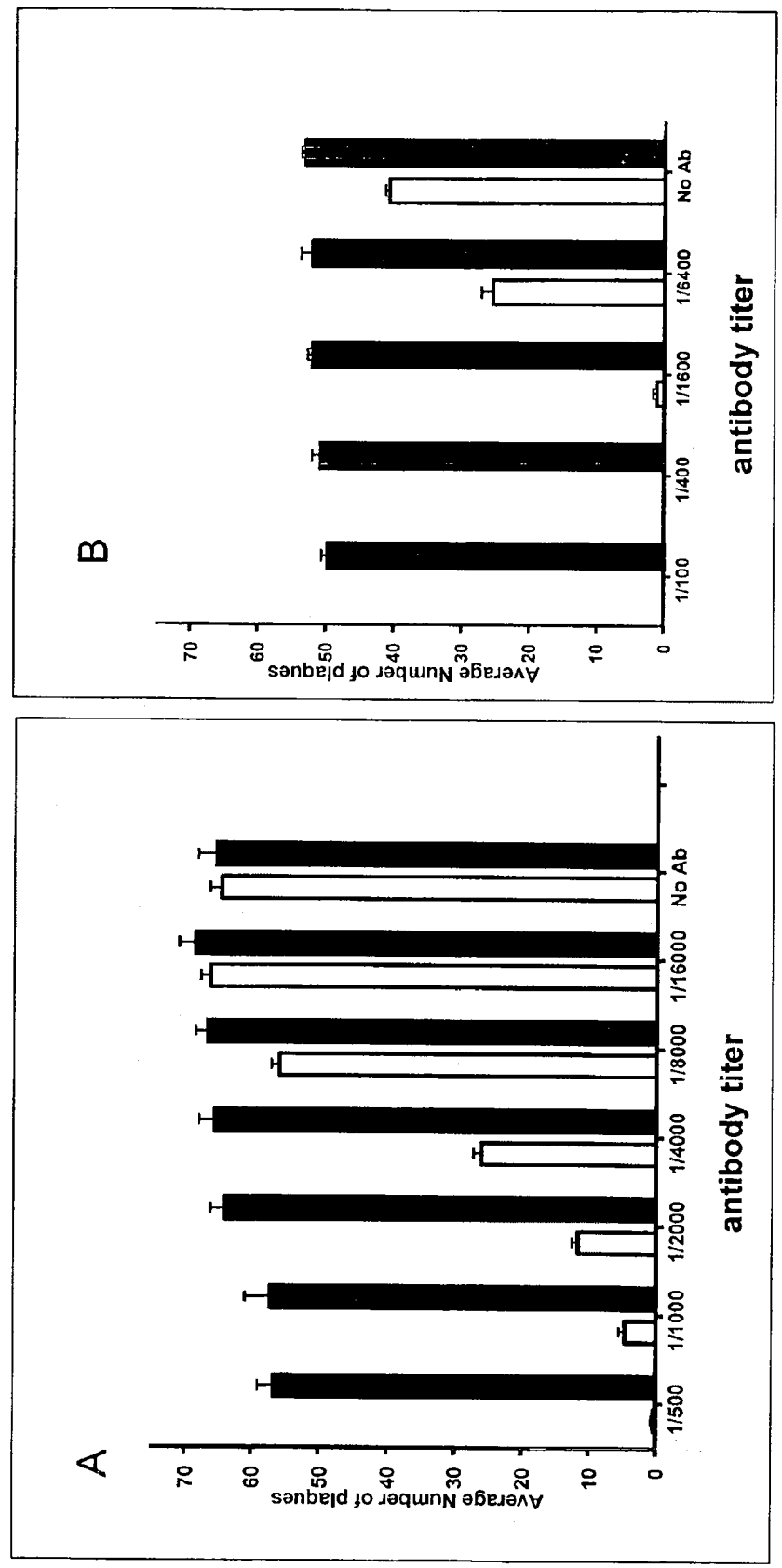

FIG. 13 is a pair of graphs showing that NimIV confers unto chimeric recombinant the neutralization characteristics of the donor serotype. FIG. 13A shows neutralization titers of CR72 (open bars) and HRV14 (black bars) with GP72 antibodies. FIG. 13B shows neutralization titers of CR6 (open bars) and HRV14 (black bars) with GP6 antibodies. Note: GP6 and GP72=guinea pig polyclonal antibodies (ATCC) against HRV6 and HRV72, respectively.

FIG. 14 is a table showing the effect of NimIV replacement on other Nims of an HRV14 backbone (NimI, II, III Mabs against HRV14, CR6 and CR72 (neutralization)).

FIG. 15 is a table showing the 50% neutralization titers of anti-CR6 and anti-CR72 mouse antiserums against HRV14, HRV6, HRV72, CR6, and CR72.

DETAILED DESCRIPTION OF THE INVENTION

In general, the invention relates to a novel immunogenic locus of human rhinovirus (HRV) and its use in vaccines to prevent or treat HRV infection. The invention is based on our discovery of a new HRV neutralizing immunogen (Nim), NimIV, which can be used as a vaccine. This vaccine, as described below, comprises several embodiments. These include single or multiple recombinant HRVs displaying heterologous NimIV antigens, synthetic NimIV peptides alone or in the context of virus, protein, or chemically-linked carriers, and mixtures of biological or chemical fusions of serotype-diverse NimIV peptides in the context of biological carriers. Such HRV vaccines, which elicit NimIV-specific immune responses to a broad array of HRV serotypes, are useful for both prophylactic and therapeutic treatment of HRV infection. The NimIV antigen, vaccine compositions including NimIV, and methods of using such compositions are described further, as follows.

Neutralizing Immunogen IV (NimIV)

Three major surface Neutralizing Immunogens (NimI, NimII, and NimIII) of rhinoviruses (HRVs) elicit highly specific neutralizing immune responses. Nim-specific antibodies block virus attachment to the cell receptor (ICAM-1). The present invention is based on the discovery of a novel Nim (NimIV), encompassing a stretch of about 17-25 amino-acid sequences at the C-terminal end of structural protein VP1, and identified by molecular evolution experiments. We demonstrate that NimIV is exchangeable between different HRV serotypes. For example, when NimIV of a donor serotype HRV (e.g., HRV6 or HRV72) is introduced into another serotype host virus (e.g., HRV14), it confers on the resulting chimeric recombinant neutralization characteristics of the donor serotype, significantly changing the neutralizing characteristics of the host virus. The incorporation of NimIV into recombinant HRV vaccines will result in serotype cross-reactive immune responses directed against a broad array of HRV serotypes.

Recombinant HRV Vaccine Utilizing Chimeric NimIV Antigens

One characteristic of an ideal HRV vaccine is the ability to protect a human at risk of HRV infection from a broad range of HRV serotypes. The vaccines of the present invention feature the ability to elicit protective and therapeutic immune responses against a large number of HRV serotypes (e.g., a majority or, more ideally, all HRV serotypes) that cause disease in humans. This can be accomplished by the use of multiple NimIV sequences in a vaccine, which can involve, for example, the addition of NimIV antigens from donor serotypes into a small group of host serotype HRVs. As we show below, the transferred NimIV antigen provokes strong neutralizing antibody responses that are serotype specific. In the context of chimeric or recombinant vaccines, the combination of a first serotype NimIV antigen into a second serotype host HRV elicits neutralizing antibodies directed against both HRV serotypes, thus broadening the protective or therapeutic benefit over a vaccine not chimeric at the NimIV locus. For example, replacement of NimIV$^{HRV14}$ (i.e., the NimIV antigen in HRV serotype 14) of HRV14 with NimIV$^{HRV6}$ yields the HRV vaccine CR6 (discussed further below). This vaccine induces generation of neutralizing antibodies directed against both. HRV14 and HRV6 serotypes. In another example, replacement of NimIV$^{HRV14}$ of HRV14 with NimIV$^{HRV72}$ yields the HRV vaccine CR72 (discussed further below). This vaccine generates neutralizing antibodies directed against both HRV14 and HRV72 serotypes. A mixture of recombinant HRVs, thus constructed, that comprise a large number of donor serotype NimIV antigens and a limited number of host serotype HRV combinations represents an ideal vaccine for the prevention or treatment of HRV infection.

NimIV Peptides

A second embodiment of the invention is the use of synthetic or naturally-derived NimIV peptides that correspond to the amino acid sequence of the NimIV genetic locus. Examples of such peptides are provided elsewhere herein (see, e.g., the Summary of the Invention and the Experimental Examples). The administration of a mixture of peptides, pooled from a broad range of HRV serotypes, elicits a broadly protective neutralizing antibody response for the prevention or treatment of HRV infection. The administration of a mixture of NimIV peptides can occur alone or in combination with pharmaceutically acceptable adjuvants or stimulants of the immune system (see below).

NimIV Fusion Molecules

Another aspect of the invention is the chemical or biological fusion of NimIV antigens to a biological carrier to be used as an HRV vaccine. In this context, NimIV peptides, derived from single or multiple serotypes, are bound to a suitable biological carrier (e.g., a hepatitis B core antigen) to improve degradation half-life, tissue penetration and specificity, detection, or immunogenicity of the NimIV peptides. Mixtures of such NimIV fusion molecules, drawn from many HRV serotypes, are then used to vaccinate a human to prevent or treat HRV infection. In other examples, NimIV peptides (which may be from many different serotypes) are cross-linked to HRV carriers.

Administration and Dosage

The present invention also provides compositions that include prophylactically or therapeutically effective amounts of one or more human rhinovirus vaccine, as described herein. The mixtures of HRV vaccines may be present in the same pharmaceutical composition (a single dosage form) or separate pharmaceutical compositions (separate dosage forms), which are administered concomitantly or at different times. The compositions can be formulated for use in a variety of drug delivery systems. One or more physiologically acceptable excipients or carriers can also be included in the compositions for proper formulation. The viruses can be in lyophilized form or dissolved in a physiologically compatible solution or buffer, such as saline or water. Standard methods of preparation and formulation can be used as described, for example, in *Remington's Pharmaceutical Sciences* (18$^{th}$ edition), ed. A. Gennaro, 1990, Mack Publishing Company, Easton, Pa.

The compositions are intended for intranasal, parenteral, topical, oral, or local administration for prophylactic and/or therapeutic treatment. Typically, the compositions are administered intranasally (e.g., by aerosol inhalation or nose drops), parenterally (e.g., by intramuscular, subcutaneous, or intravenous injection), or by oral ingestion, or by topical application or intraarticular injection. Additional routes of administration include intravascular, intra-arterial, intratumor, intraperitoneal, intraventricular, intraepidural, as well as ophthalmic, intrascleral, intraorbital, rectal, or topical administration. Sustained release administration is also specifically included in the invention, by such means as depot injections or erodible implants or components. Thus, the invention provides compositions for mucosal or parenteral administration that include the above-mentioned agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Further, this invention provides compositions for local administration, which may contain inert ingredients such as solvents or emulsifiers for the formulation of a cream, an ointment, and the like.

These compositions may be sterilized by conventional sterilization techniques, or may be sterile filtered. The resulting aqueous solutions may be packaged for use as is or lyophilized, the lyophilized preparation being combined with a sterile aqueous carrier prior to administration. The pH of the preparations typically will be between 3 and 11, e.g., between 5 and 9, 6 and 8, or 7 and 8, such as 7 to 7.5. The resulting compositions in solid form may be packaged in multiple single dose units, each containing a fixed amount of the above-mentioned agent or agents, such as in a sealed package of tablets or capsules. The compositions can also include the active ingredient(s) in lyophilized form, which is reconstituted for administration.

The compositions containing an effective amount of vaccine can be administered for prophylactic and/or therapeutic treatments. In prophylactic applications, compositions can be administered to a subject (e.g., a human subject) with increased susceptibility to HRV infection. Compositions of the invention will be administered to the subject (e.g., a human) in an amount sufficient to delay, reduce, or prevent the onset of clinical or subclinical disease. In therapeutic applications, compositions are administered to a patient (e.g., a human) already suffering from HRV infection in an amount sufficient to cure or at least partially arrest the symptoms of the condition and its complications. An amount adequate to accomplish this purpose is defined as a "therapeutically effective dose." Determination of an appropriate dosage amount and regimen can readily be determined by those of skill in the art. Amounts effective for this use may depend on the severity of the disease or condition and the weight and general state of the patient, but generally range from about 0.5 mg to about 3000 mg of the agent or agents per dose per patient. The vaccines can be administered one time only or in prime/boost regimens. Suitable regimens for initial administration and booster administrations are typified by an initial administration followed by repeated doses at one or more hourly, daily, weekly, or monthly intervals by a subsequent administration. The total effective amount of an agent present in the compositions of the invention can be administered to a mammal as a single dose, either as a bolus or by infusion over a relatively short period of time, or can be administered using a fractionated treatment protocol, in which multiple doses are administered over a more prolonged period of time (e.g., a dose every 4-6, 8-12, 14-16, or 18-24 hours, or every 2-4 days, 1-2 weeks, once a month).

The therapeutically-effective amount of one or more agents present within the compositions of the invention and used in the methods of this invention applied to mammals (e.g., humans) can be determined by the those of skill in the art with consideration of individual differences in age, weight, immune system integrity, and the condition of the mammal. The agents of the invention are administered to a subject (e.g. a mammal, such as human, mouse, livestock (e.g., cattle, sheep, or pigs), domestic pet (e.g., cat or dog)) in an effective amount, which is an amount that produces a desirable result in a treated subject (e.g., the prevention of HRV infection in a susceptible individual or the lessening of symptoms in an infected individual). Such therapeutically effective amounts can be determined empirically by those of skill in the art.

The vaccines of the invention can be used in combination with other vaccination approaches, as well as other approaches to treatment (e.g., small molecule-based approaches). For example, the viruses can be administered in combination with other recombinant vaccines including the same or different antigens. The combination methods of the invention can include co-administration of vaccines of the invention with other forms of the antigen. Alternatively, the vaccines of the present invention can be used in combination with other approaches (such as subunit or HBc approaches (HBc-M2e; Fiers et al., Virus Res. 103:173-176, 2004; WO 2005/055957; US 2003/0138769 A1; US 2004/0146524A1; US 2007/0036826 A1)) in a prime-boost strategy, with either the vaccines of the invention or the other approaches being used as the prime, followed by use of the other approach as the boost, or the reverse. Further, the invention includes prime-boost strategies employing the vaccine of the present invention as both prime and boost agents.

The vaccines of the invention can be administered to subjects, such as mammals (e.g., human subjects) using standard methods. In the case of intranasal administration, the vectors can be administered in the form of nose-drops or by inhalation of an aerosolized or nebulized formulation.

The vectors of the invention can be administered to subjects, such as humans, as live or killed vaccines. The live vaccines can be administered intranasally using methods known to those of skill in the art (see, e.g., Grunberg et al., Am. J. Respir. Crit. Car. Med. 156:609-616, 1997). Appropriate dosage amounts and regimens can readily be determined by those of skill in the art. As an example, the dose range can be, e.g., $10^3$ to $10^8$ pfu per dose. The vaccine can advantageously be administered in a single dose, however, boosting can be carried out as well, if determined to be necessary by those skilled in the art. As to inactivated vaccines, the virus can be killed with, e.g., formalin or UV treatment, and administered intranasally at about $10^8$ pfu per dose, optionally with appropriate adjuvant (e.g., chitin or mutant LT; see above). In such approaches, it may be advantageous to administer more than one (e.g., 2-3) dose.

The size of the peptide or protein that is included in a vaccine of the invention can range in length from, for example, from 3-1000 amino acids, for example, from 5-500, 10-100, 20-55, 25-45, or 35-40 amino acids, as can be determined to be appropriate by those of skill in the art. Thus, peptides in the range of 7-25, 12-22, and 15-20 amino acids in length can be used in the invention. Further, the peptides noted herein can include additional sequences or can be reduced in length, also as can be determined to be appropriate by those skilled in the art. The peptides listed herein can be present in the vectors of the invention as shown herein, or can be modified by, e.g., substitution or deletion of one or more amino acids (e.g., 1, 2, 3, 4, 5, 6, 7, 8, 9, 10, or more amino acids). In addition, the peptides can be present in the vaccine in the context of larger peptides. Optionally, peptides such as those described above and elsewhere herein include additional sequences on the amino and/or carboxyl terminal ends, whether such sequences are naturally associated with the peptide sequences (i.e., the sequences with which the peptides are contiguous in the influenza virus genome) or not (e.g., synthetic linker sequences). The peptides can thus include, e.g., 1-25, 2-20, 3-15, 4-10, or 4-8 amino acid sequences on one or both ends. As a specific example, the peptide may include 1-3 linker sequences at amino and/or carboxyl terminal ends.

Adjuvants

For vaccine applications, optionally, adjuvants that are known to those skilled in the art can be used. Adjuvants are selected based on the route of administration. In the case of intranasal administration, chitin microparticles (CMP) can be used (Asahi-Ozaki et al., Microbes and Infection 8:2706-2714, 2006; Ozdemir et al., Clinical and Experimental Allergy 36:960-968, 2006; Strong et al., Clinical and Experimental Allergy 32:1794-1800, 2002). Other adjuvants suitable for use in administration via the mucosal route (e.g., intranasal or oral routes) include the heat-labile toxin of E. coli (LT) or mutant derivatives thereof. In the case of inactivated virus, parenteral adjuvants can be used including, for example, aluminum compounds (e.g., an aluminum hydroxide, aluminum phosphate, or aluminum hydroxyphosphate compound), liposomal formulations, synthetic adjuvants, such as (e.g., QS21), muramyl dipeptide, monophosphoryl lipid A, or polyphosphazine. In addition, genes encoding cytokines that have adjuvant activities can be inserted into the vectors. Thus, genes encoding cytokines, such as GM-CSF, IL-2, IL-12, IL-13, or IL-5, can be inserted together with foreign antigen genes to produce a vaccine that results in enhanced immune responses, or to modulate immunity directed more specifically towards cellular, humoral, or mucosal responses. Alternatively, cytokines can be delivered, simultaneously or sequentially, separately from a recombinant vaccine virus by means that are well known (e.g., direct inoculation, naked DNA, in a viral vector, etc.).

EXPERIMENTAL EXAMPLES

Identification of NimIV

We have discovered a neutralizing immunogen, NimIV, which encompasses a 17-25 amino acid long, non-conserved sequence of the C-terminus of virus structural protein 1 (VP 1). This epitope can be exchanged between HRV serotypes. If substituted, NimIV confers its neutralization characteristics to the heterologous HRV. Synthetic peptides corresponding to NimIV were shown to be recognized by virus-specific antibodies in ELISA and Western blot experiments.

Two viable chimeras HRV14-NimIV$^{HRV6}$ (CR6) and HRV14-NimIV$^{HRV72}$ (CR72) were isolated during a molecular evolution experiment (VP1 gene shuffling) performed as described below. As shown in the alignment presented in FIG. 12A, VP1 sequences of CR6 and CR72 included several individual amino acid substitutions as well as replacements of NimIV$^{HRV14}$ to NimIV$^{HRV6}$ and NimIV$^{HRV72}$ in CR6 and CR72 respectively. NimIVs alignment (FIG. 12B) showed that all NimIV viruses contain conservative central domain (PVIKKRK/E), while flanking regions were varied. Interestingly, amino acids at positions 279 and 282 were shown to be fully conserved or similar within all HRV serotypes (RM2506). CR6 and CR72 chimeras were shown to be strongly neutralized with polyclonal guinea pig antibodies GP6 and GP72 (ATCC), while neither of these antibodies neutralized backbone virus (HRV14; FIG. 13). Mouse polyclonal antibodies derived against HRV6 and HRV72 were also shown to neutralize CR6 and CR72 at 10 fold lower titer then GP6 or GP72. evidenced that NimIV determinants in CR6 and CR72 are surface exposed and in favorable conformation for neutralizing antibody binding. Conformation of these epitopes in chimeras most possibly corresponds to that in wild type viruses.

DNA Shuffling as a Method of Isolation of NimIV Replacement

Figure 1:
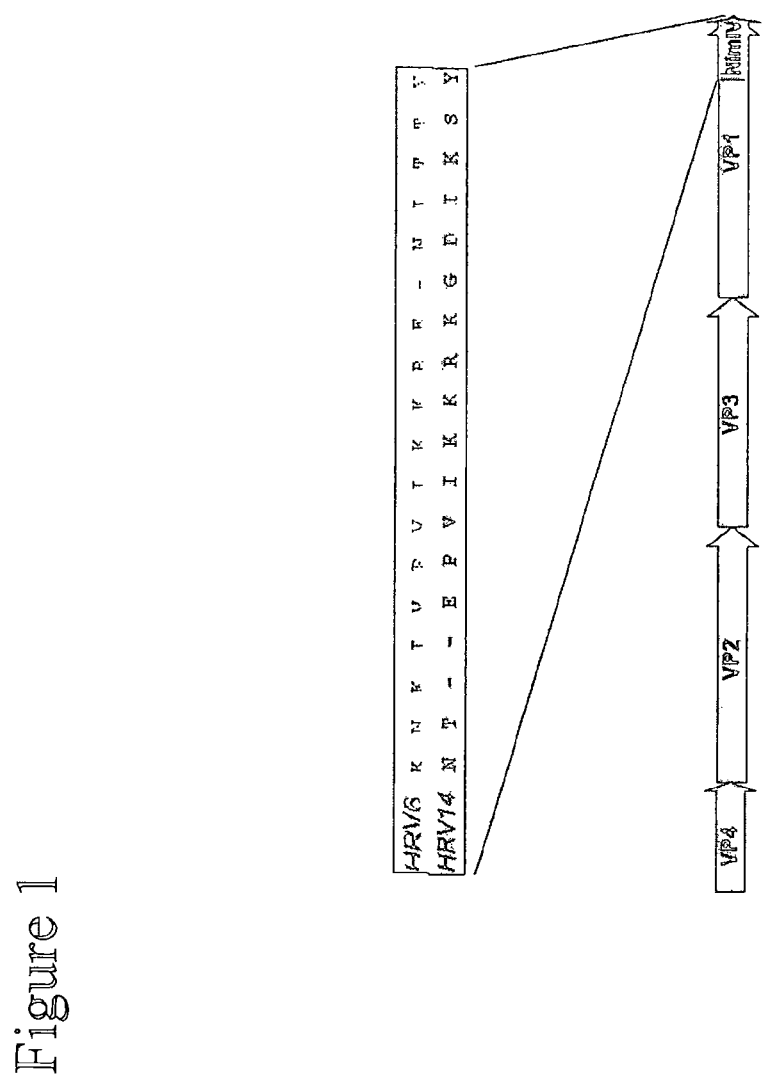

Discovery of NimIV was possible after the generation of HRV chimera CR6 carrying the replacement of 18 amino acids of the C-terminus part of VP1 with the corresponding 17 amino acid region of HRV6 (see FIG. 1). This sequence was obtained by DNA shuffling (for method review see Patten et al., "Applications of DNA shuffling to pharmaceuticals and vaccines," *Curr Opin Biotechnol* 8:724-733 (1997); examples of use include Zhang et al., "Broadly cross-reactive mimotope of hypervariable region 1 of hepatitis C virus derived from DNA shuffling and screened by phage display library," *J Med Virol* 71:511-517 (2003), Castle, et al., "Discovery and directed evolution of a glyphosate tolerance gene," *Science* 304:1151-1154 (2004), Pekrun et al., "Evolution of a human immunodeficiency virus type 1 variant with enhanced replication in pig-tailed macaque cells by DNA shuffling," *J Virol* 76:2924-2935 (2002), Toth et al., "Improvement of the movement and host range properties of a plant virus vector through DNA shuffling," *Plant J* 30:593-600 (2002), Kaper et al., "DNA family shuffling of hyperthermostable beta-glycosidases," *Biochem J* 368:461-470 (2002). Wang et al., "Directed evolution of substrate-optimized GroEL/S chaperonins," *Cell* 111:1027-1039 (2002), and Hurt et al., "Highly specific zinc finger proteins obtained by directed domain shuffling and cell-based selection," *Proc Natl Acad Sci U.S.A.* 100:12271-12276 (2003)), followed by cloning this fragment back into HRV14 infectious clone. Approximately 100 VP1 sequences were included in the DNA shuffling experiment (Ledford et al., "VP1 sequencing of all human rhinovirus serotypes: insights into genus phylogeny and susceptibility to antiviral capsid-binding compounds," *J Virol* 78:3663-3674 (2004)).

CR6 is Neutralized by Both GP6 and GP14

Figure 2:
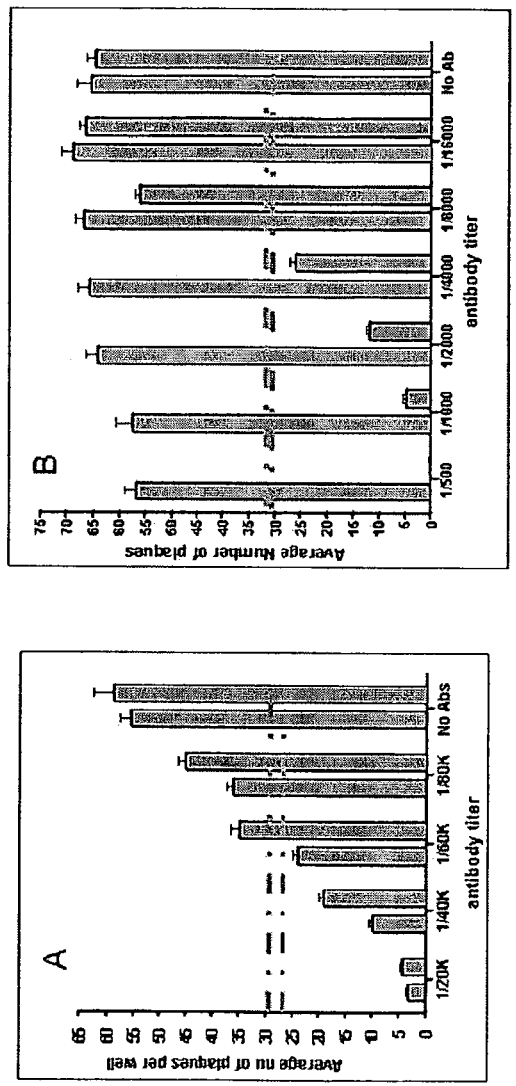

The neutralization specificity of the CR6 chimera was shown to be different from parental HRV14 vector (pWR3.26 infectious clone). In addition to neutralization detected with HRV14-specific polyclonal guinea pig Abs (GP14; FIG. 2A) we found neutralization of CR6 with guinea pig HRV6-specific antibodies (GP6; FIG. 2B), whereas the parental HRV14 is not neutralized with GP6 (FIG. 2). This indicates that the C-terminus domain of HRV6 is immunogenic and neutralizing.

Figure 8:
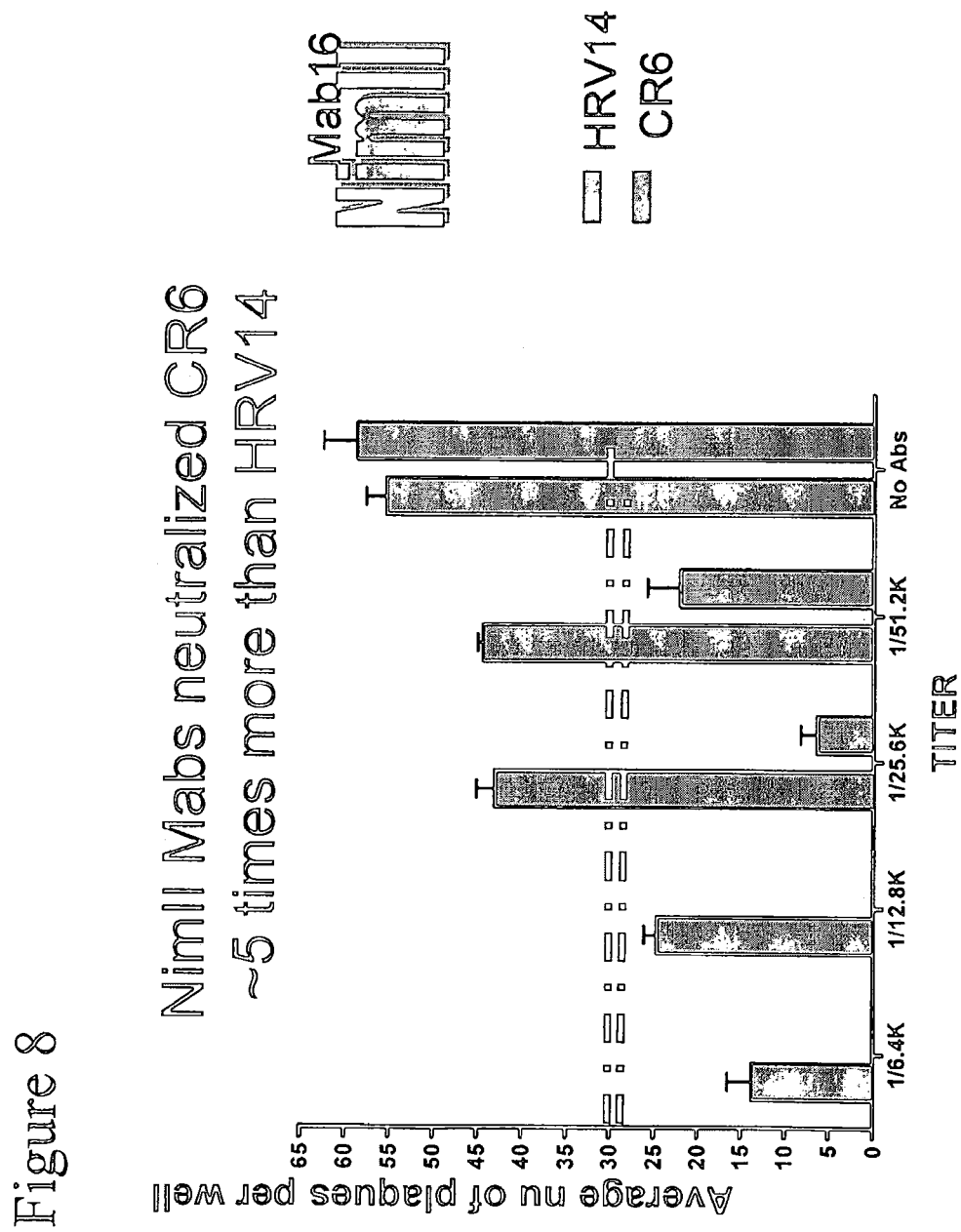
FIG. 8 is a graph showing the results of plaque reduction neutralization test (PRNT) studies of HRV14 and CR6, which shows that a NimII monoclonal antibody (Mab16) neutralized CR6 about five fold more than HRV14.
Figure 9:
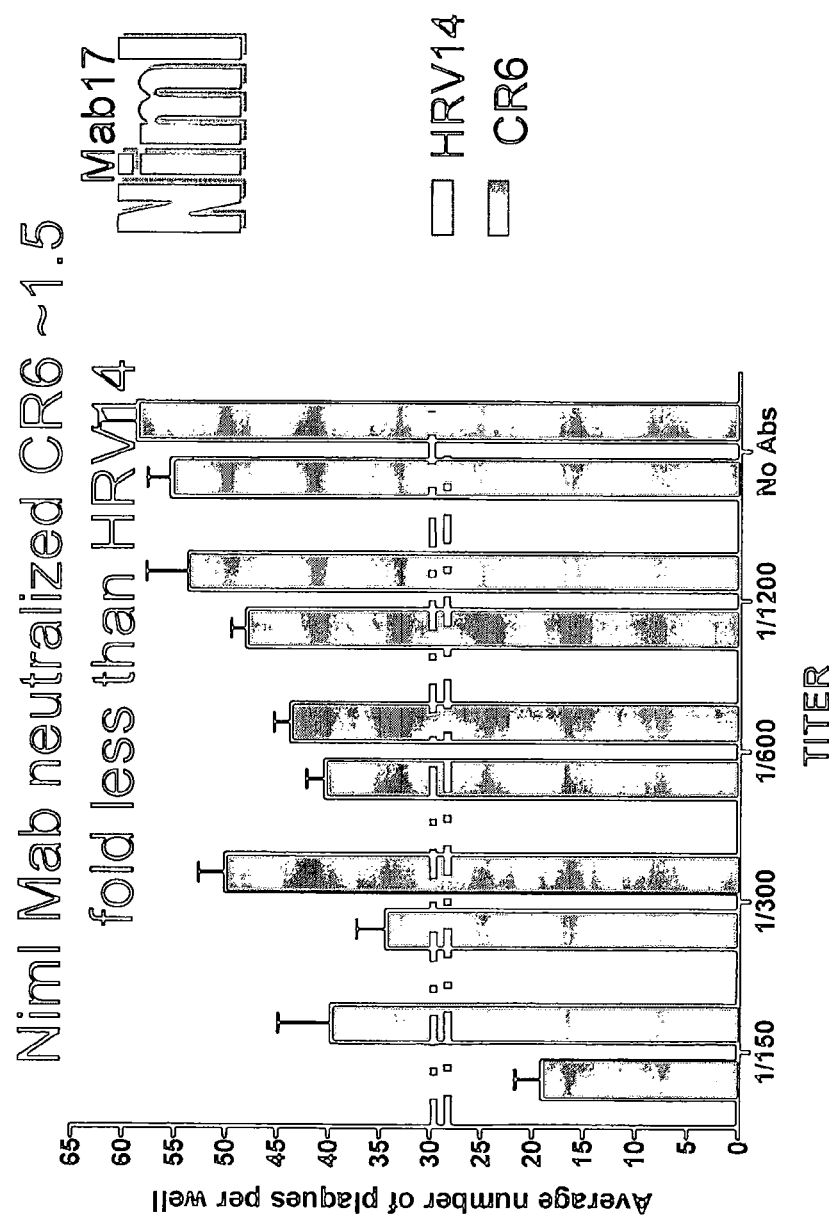
FIG. 9 is a graph showing the results of plaque reduction neutralization test (PRNT) studies of HRV14 and CR6, which shows that a NimI monoclonal antibody (Mab17) neutralized CR6 about 1.5 fold less than HRV14.

CR6 is Strongly Neutralized by NimI- and NimII-, but not by NimIII-Specific mAbs The presence of NimIV$^{HRV6}$ in HRV14 background (CR6) changes NA of other Nims (HRV14). PRNTs with Nim$^{HRV14}$-specific mAbs revealed that CR6 NimIII-specific neutralization was decreased (~10 fold; FIG. 7), whereas NimII-specific NA was increased (5 fold; FIG. 8); NimI-specific neutralization was only slightly affected (1.5 fold; FIGS. 9 and 16). These findings are summarized in FIG. 10.

Effect of NimIV$^{HRV6\ and\ HRV72}$ on Neutralizing Potency of Backbone Nims

To study effect of NimIV replacements on neutralizing characteristics of backbone Nims a panel of HRV14 Nim-specific mouse monoclonal antibodies were used against CR6 and CR72 (FIG. 14). Neutralizing ability of NimI of both chimeras was only slightly if at all affected, whereas NimII and NimIII of CR6 demonstrated 5 fold higher and 10 fold lower neutralization rates, respectively. In contrast NimIII-dependent neutralization of CR72 was not affected. Unfortunately neutralization of CR72 with NimII-specific antibodies was not studied since of limit of antibody supply. These data evidenced for strong interaction between NimIV and NimIII domains which are consistent with crystallography and previously obtained mutagenesis data.

Modeling of Interactions of NimIV with Other Nims within CR6 and HRV14

Figure 3:
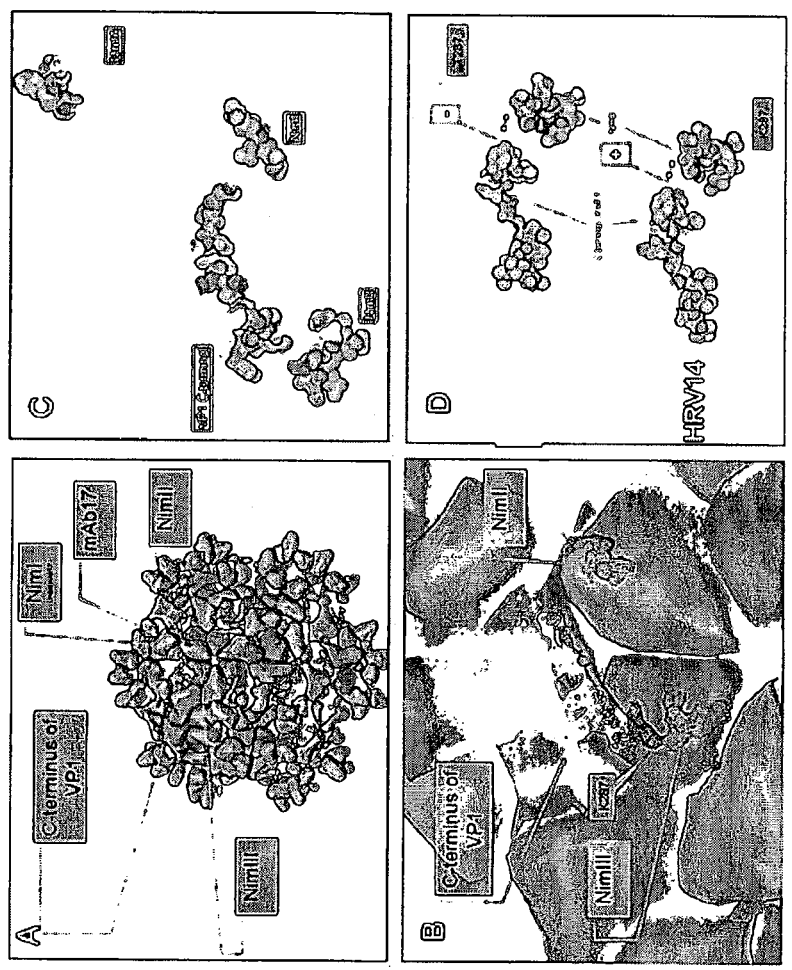

These results demonstrate the importance of NimIV HRV6 for conformational integrity of CR6. 3D modeling was performed on the basis of known crystal structure (Che et al., "Antibody-mediated neutralization of human rhinovirus 14 explored by means of cryoelectron microscopy and X-ray crystallography of virus-Fab complexes," *J Virol* 72:4610-4622 (1998) revealed a close contact of NimIII with NimIV in HRV14, but not in CR6 particles (FIG. 3 B, D). This contact in HRV14 was associated with positive charge of K287 of VP1 through which it interacted with negatively charged residues of NimIII (FIG. 3 B, D). In CR6, mutation to T 287 abrogates this connection (FIG. 3D). Interestingly, the negative effect of mutation at K287 on NimIII-specific neutralization was documented previously (Sherry et al., "Use of monoclonal antibodies to identify four neutralization immunogens on a common cold picornavirus, human rhinovirus," *J Virol* 57:246-257 1986)), but the authors claimed that C-terminal region of VP 1 was not a neutralizing immunogen (Nim) due to the absence of escape mutants to neutralization with monoclonal antibodies specific to that region. NimIV$^{HRV6}$ in CR6 only slightly affects NimI-specific neutralization, which could be partially explained by bigger distance of this epitope from NimIV (FIG. 3C).

A unique feature of CR6 is its 5 fold higher sensitivity to NimII-specific neutralization (FIG. 14). This enhancement could not be explained by direct physical contact of NimIV$^{HRV6}$ and NimII$^{HRV14}$. 3D modeling revealed distant localization of these Nims in virus particle (FIGS. 3A-C). Most likely this phenomenon could be explained by conformational changes in VP2, which possibly led to more favorable to monoclonal antibody binding exposure of NimII on the surface of virus particle.

Cross-Neutralization Profile of CR6

Figure 4:
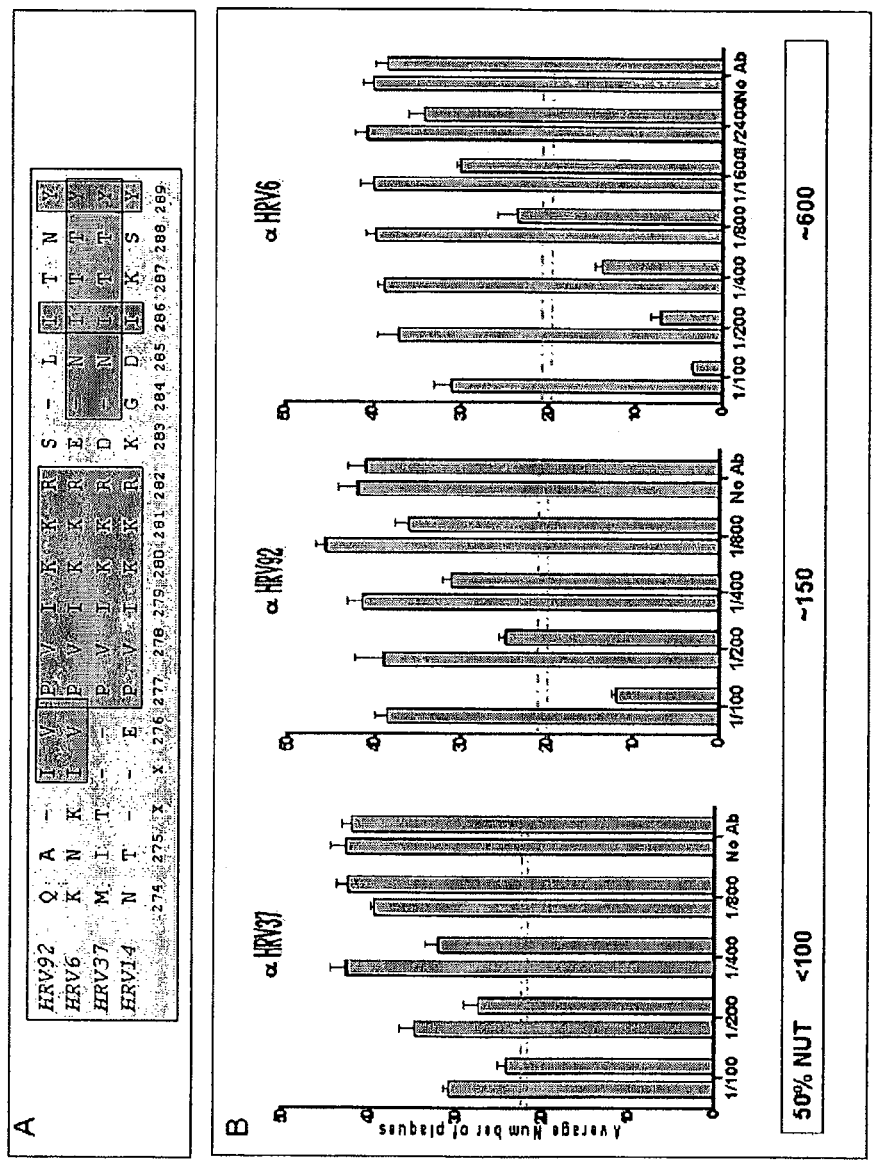
Figure 6:
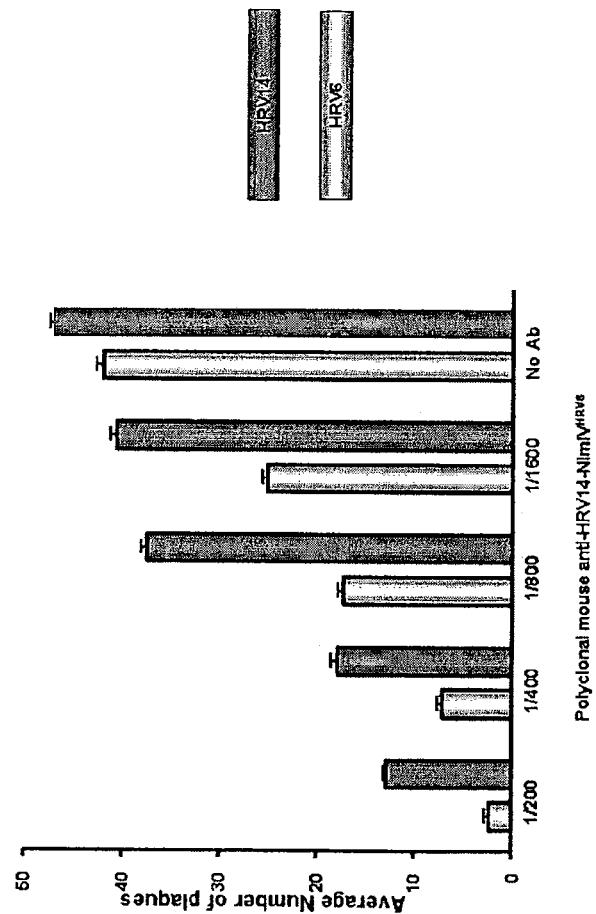
FIG. 6 is a graph showing the results of plaque reduction neutralization test (PRNT) studies of HRV14 and HRV6 with mouse anti-HRV14-NimIV$^{HRV6}$ serum. These data show immunodominance of NimIV$^{HRV6}$ in the background of HRV14 capsid.
Figure 11:
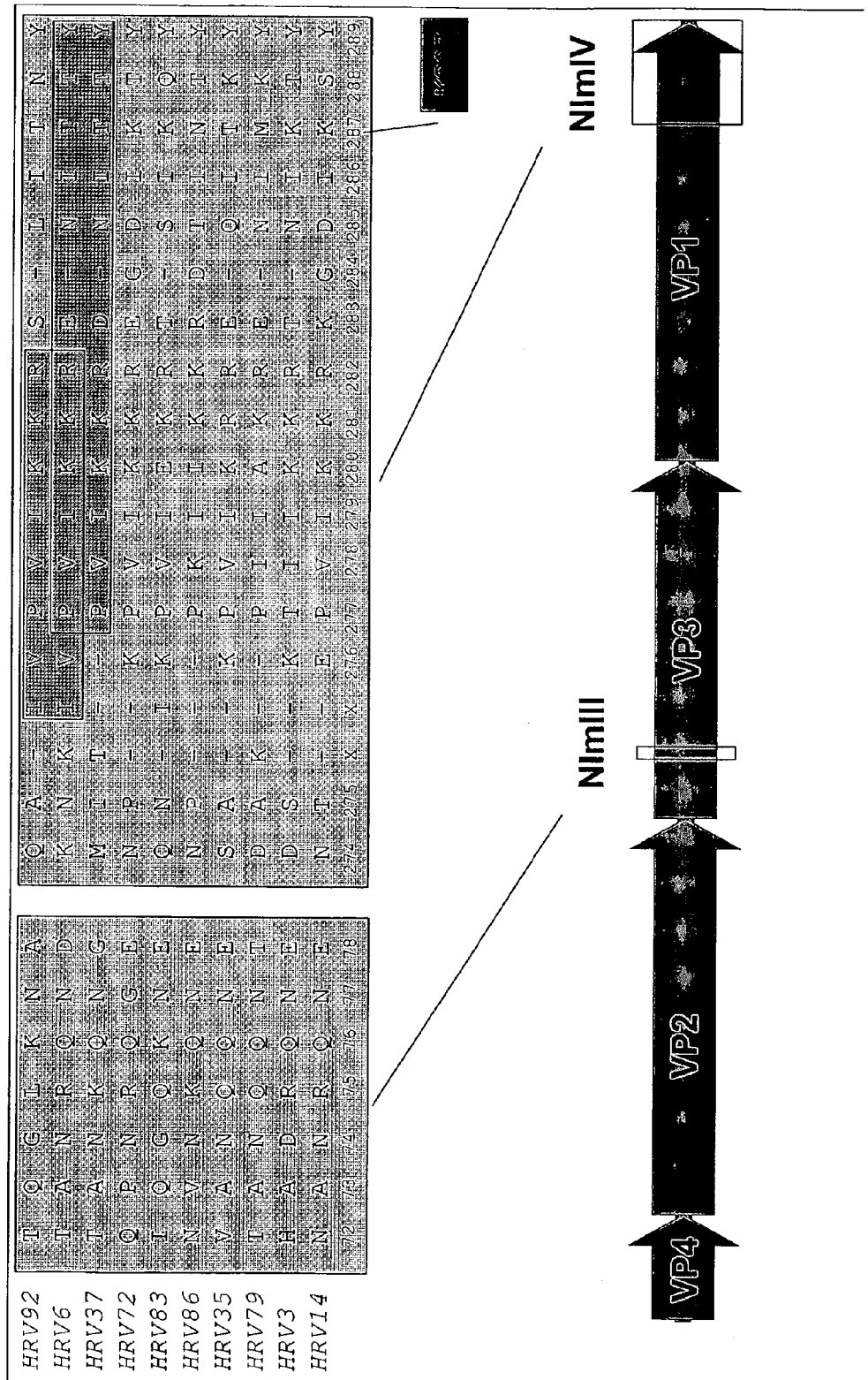
FIG. 11 shows an alignment of NimIII and NimIV sequences (SEQ ID NOS: 10, 18, and 20-37), as well as the position of these sequences in the HRV structural proteins.

The alignment of NimIV$^{HRV6}$ with NimIV of all 100 serotypes identified its two closest matches: C-terminal ends of HRV37 and HRV92 (see FIG. 4A). Analysis revealed the presence of three regions within NimIV: conservative (core) region consisting of 6 AA (P-V-I-K-K-R) and two regions upstream and downstream from core. Core was also detected in NimIVs of 7 closely related viruses (HRV14, HRV72, HRV83, HRV86, HRV35, HRV79, and HRV3; see FIG. 11). It is worth to note here that R282 was found to be conservative among all 100 HRV serotypes. As is shown in FIG. 4A, 6 AA of downstream regions of NimIV$^{HRV6}$ and NimIV$^{HRV37}$ are almost identical (D/E-N-I-T-T-Y), whereas corresponding sequence of HRV92 is quite different (S-L-I-T-N-Y) from them. Upstream regions of NimIV$^{HRV6}$ and NimIV$^{HRV92}$ have two identical amino acids, whereas the corresponding region of NimIV$^{HRV37}$ exposes no apparent similarity with NimIV$^{HRV6}$. This difference between NimIVs provided an opportunity to assess which portion of the epitope is important for neutralization of CR6 virus. To study this we generated mouse convalescent sera against all three serotypes and tested them for neutralization of CR6 (FIG. 4B). In spite of extensive homology between downstream regions of NimIV$^{HRV6}$ and NimIV$^{HRV37}$ anti-HRV37, sera revealed no neutralization, confirming the insignificance of the downstream region for neutralization. Conversely, anti-HRV92 sera demonstrated only slightly decreased NA than anti-HRV6. None of these three sera samples was able to neutralize HRV14. These results represent a functional dissection of NimIV, providing evidence for higher cross-neutralization activity of upstream versus core and downstream regions. To answer the question of whether differential recognition of these viruses by mouse antibodies reflects their real interaction with NimIV-specific sequences, we synthesized NimIV$^{HRV14}$ and NimIV$^{HRV6}$-specific peptides and performed Western and ELISA assays with the same set of antibodies.

Figure 5:
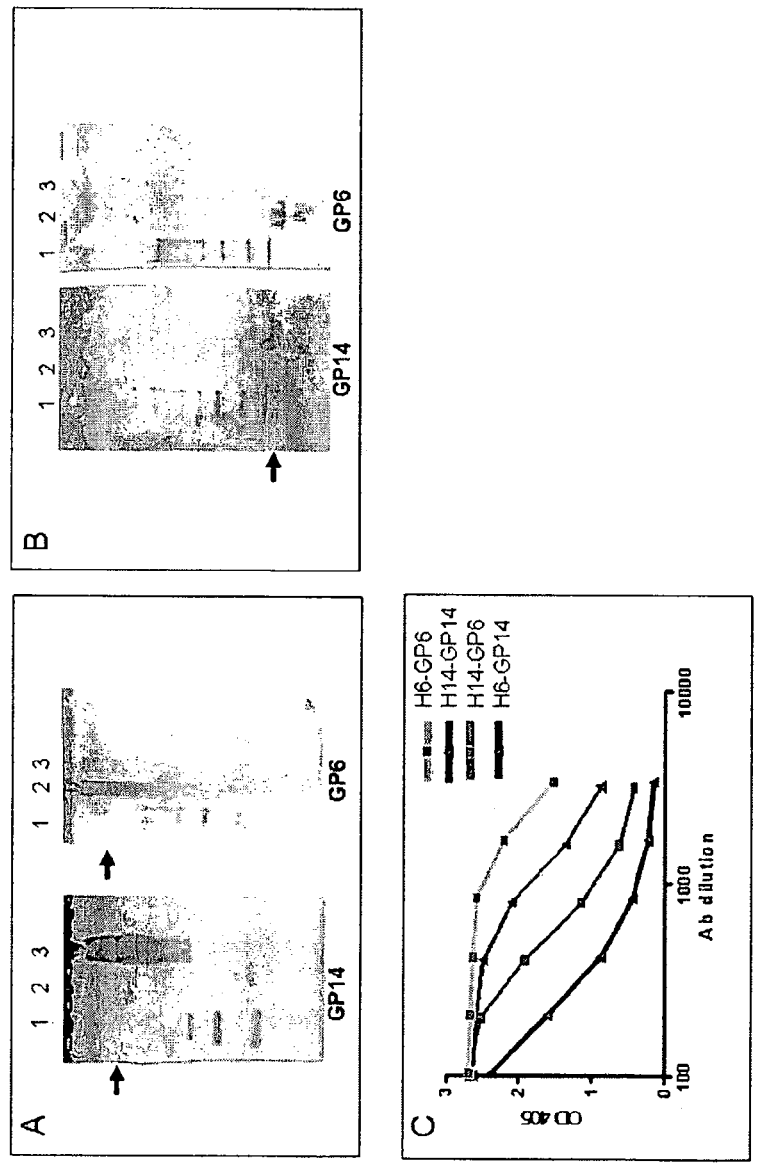

Immunoreactivity of NimIV-Specific Peptides GP14 and GP6 Differentiate Between Serotype Specific Peptides Gp6 and GP14 recognize specifically homologous NimIV-specific peptides in Western blot (FIG. 5A-B) and ELISA (FIG. 5C) assays. FIGS. 5A and 5B represent Western blot results with KLH-bound materials and free peptides respectively. Due to the high molecular weight of KLH (~3×10$^5$ kDa) the protein bands on FIG. 5A appear smeared. The immunoreactivity of given peptides are very specific since no signals were detected with heterologous combinations of peptide/antibody (GP6/NimIV$^{HRV14}$ or GP14/NimIV$^{HRV6}$). Traces of signal in heterologous combinations in KLH-bound material are attributed to features of KLH. These results are evidencing about linearity and high specificity of NimIV epitopes on the surface of HRV6 and HRV14 purified samples of which were used for generating GP6 and GP14, respectively. No apparent cross-reactivity between these peptides witnessed about low immunogenicity of core part of these Nims. If this statement were not true, high cross-immunoreactivity should be seen in this experiment.

High specificity of recognition of these peptides with GP6 and GP14 is also confirmed by ELISA (FIG. 5C). Lower reactivity of H14 with GP14, then H6 with GP6 could indicate on the difference in NimIV epitope presentation on the surfaces of virus particles. These results are reciprocal to PRNT data described in FIG. 2. In both experiments no apparent cross-reactivity between HRV14 and HRV6 or their NimIV-specific peptides was identified.

In vivo Studies: Anti-CR6 Serum Neutralizes HRV6

11-12 week old female Blb/c mice were immunized three times (on days 1, 14, and 28) intraperitoneally with either virus suspensions (10$^5$ pfu/ml) mixed with adjuvant (aluminum hydroxide), or mock (diluent), in a 100 µl volume. Mice were terminally bled on day 49. To test for serum antibody levels, mice were bled prior to inoculation (baseline) and on day 30-40 after immunization via the retro-orbital route under isofluorane inhalation anesthesia or via mandibular route without anesthesia (volume no more than 7.7 µl/g body weight). PRNT assay demonstrated specific neutralization of HRV6 with the serum pool from 2 mice (FIG. 6). It also showed decreased neutralization of HRV14 virus, which provides evidence that NimIV$^{HRV6}$ in CR6 is the immunodominant epitope.

Methods

Peptides and Conjugates

Oligopeptides NimIV$^{HRV6}$, Nim$^{HRV72}$, and NimIV$^{HRV14}$ corresponding to C-terminal ends of structural regions of HRV6 (CKNIVPVIKKRENITTY), HRV14 (CNTEPVIKKRKGDIKSY) and HRV72 (CNPKPVIKKREGDIKTY) respectively were prepared by standard solid-phase synthesis by Biosynthesis, Inc (Lewisville, Tex.). Part of peptide materials were conjugated to a Hemocyanin from *Concholepas concholepas* (KLH) by use of crosslinker succinimidyl-4-(p-maleimidophenyl)-butyrate (sMBS) and reducing agent TCEP.HCl Tris(2-carboxyethyl)phosphine hydrochloride (TCEP HCL).

Cell Culture, Viral Propagation and Reagents

HRV serotypes 6, 14, 35, 37, 72, 83, 86, 92 stocks (ATCC) were amplified to high titer by successive infection of target H1 HeLa cells. HeLa cells (ATCC) were maintained in Minimum Essential Medium (Invitrogen) with 5% fetal bovine serum (JRH Biosciences, KS) for routine propagation. Cells were maintained under subconfluent growth conditions during passage. After 48 hours at 34° C., viruses were released from the cells by three freeze-thaw cycles at −80 and 37° C. The cell debris was discarded, while supernatant containing amplified virus was aliquoted and frozen at −80° C. Guinea pig antiserum for HRV serotypes 6, 14, 72, 92, and 37 were obtained from the ATCC.

VP1 Gene Shuffling Virus Libraries

Figure 12:
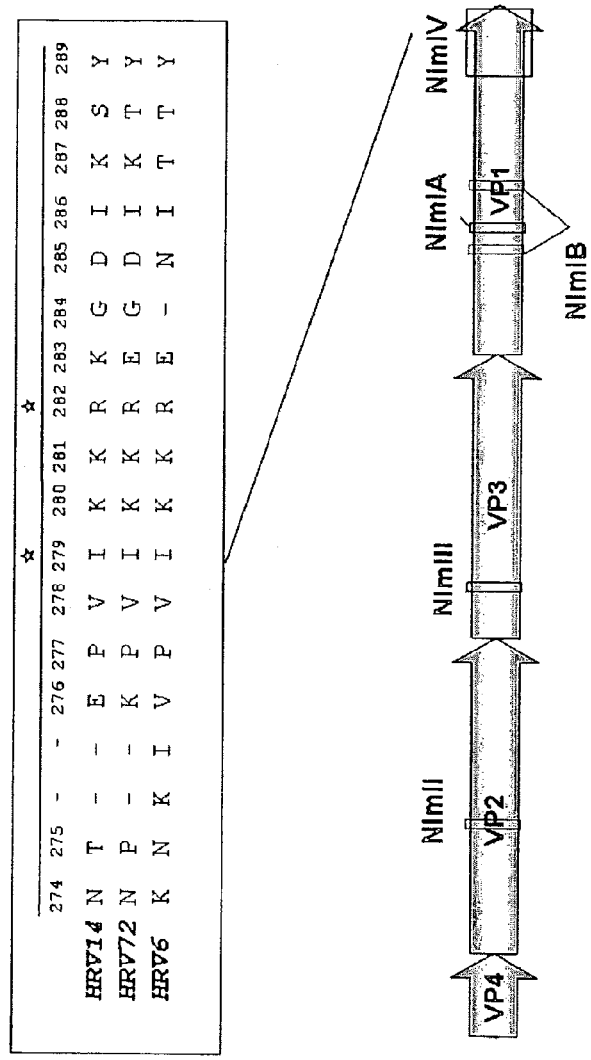
FIG. 12A is an alignment of VP1 sequences (SEQ ID NOS: 38-40) of CR6 and CR72 chimeras.
FIG. 12B is a schematic representation of HRV genome, with alignment of NimIVs of HRV6 (SEQ ID NO: 18), HRV72 (SEQ ID NO: 32), and HRV14 (SEQ ID NO: 10).

DNA fragments of VP1 are amplified by RT-PCR from RNA of HRV serotypes 6, 14, 35, 37, 72, 79, 83, 86, and 92. For the purpose of further cloning internal AvrII sites presented in VP1 genes of HRV serotypes 83, 86, 92 are removed by virtue of recombinant PCR. All PCR fragments are pooled together and shuffled, followed by cloning in modified HRV14 cDNA vector pWR3.26 (ATCC). Briefly, two microgram of pooled PCR fragments are treated with DNase I (Amersham Pharmacia Biotech, Inc) and a fraction of 50-100 bp DNA fragments is gel purified and subjected to 15-25 cycles of PCR without primers at 94° C. 30 sec, 50° C. 1 min, 72° C. 1 min followed by 25 cycles PCR with cloning primers at 94° C. 30 sec, 55° C. 30 sec, 72° C. 1 min. Library of amplified shuffled VP1 sequence are cloned into the modified pWR3.26 plasmid at XhoI and AvrII site. For that purpose HRV14 cDNA clone pWR3.26 is modified by inserting XhoI site at 5' site of VP1 sequence (FIG. 12). XhoI and AvrII sites are incorporated into VP1 forward and reverse cloning primers respectively.

VP1 shuffling plasmid DNA library is linearized by MluI digestion and transcribed in vitro by T7 transcription kit (Epicentere, Inc). RNA is transfected into H1-Hela cell (ATCC) by lipofectine (Invitrogen, Inc). Cells are harvested after incubation at 34° C. for 2-4 days. Cell samples are subjected to three freeze-thaw cycles and the supernatant is used to infect monolayer of H1-Hela cells. Virus library are stored at −80° C.

Isolation of HRV14-NimIV Recombinant Viruses

HRV14-NimIV$^{HRV6}$ (CR6) chimera is plaque purified from virus library described above. To isolate other HRV14-NimIV$^{HRVX}$ recombinants total RNA from virus library is used as a template for 8 different RT-PCR reactions performed with 8 serotype-specific reverse primers annealing to 3'-ends of VP1 gene. The same forward primer complimentary to conservative region upstream to VP1 gene was used in all of these reactions. Resulting PCR fragments are cloned back into pWR3.26 plasmid as described above for VP1 shuffliants. After transcription and transfection into H1 Hela cells, individual viruses are plaque purified and sequenced.

Animal Protocols 8 week old female Balb/c mice (10 mice per group) are primed on day 0, then boosted on days 14 and 28 by intraperitoneal administration of filtered cell culture medium containing ~1.0×10$^6$ pfu per dose of either (1) HRV14-NimIV$^{HRV6}$, (2) HRV14-NimIV$^{HRV72}$, (3) parental HRV14, or mock (culture supernatant) as a negative control, mixed with 100 µg of adjuvant (aluminum hydroxide) in a 500 µL volume.

NimIV$^{HRV6}$ and NimIV$^{HRV6}$, coupled (or not) to KLH peptides are used for immunization of 8 week old female Balb/c mice. Mice are primed on day 0 with 100 µl of 15 µg of KLH-bound peptide in Titermax Gold (1:1 emulsion) via the subcutaneous route and boosted twice (on day 36 and day 49) by intraperitoneal administration of 15 µg of "free" peptides dissolved in 100 µl of PBS.

NimIV-specific antibody titers in sera are determined by an established ELISA performed in microtiter plates coated with corresponding synthetic NimIV peptides.

Plaque Reduction Neutralization Test (PRNT)

Approximately 50 pfu of studied HRV (in complete MEM+5% FBS culture medium) is mixed with various dilutions of sample serum in a total volume of 3004 and incubated overnight at 4° C. One hundred microliters of each mixture is used to infect one well of H1 Hela cells in a 12 wells tissue culture plate (seeded at 6×10⁵ H1-HeLa cells per well and incubated overnight in a 37° C. incubator). After 1 h incubation at 34° C., the cells are overlaid with 1 mL of 0.4% agarose in MEM, 10% FBS with Pen/Strep and incubated at 34° C. for approximately 3 days. The monolayers are then fixed with formaldehyde (3.7% final concentration) and stained with 1% crystal violet in 70% methanol.

ELISA 96 well plates are coated with 5 μg/ml of NimIV-specific peptides or purified HRV14 virus for overnight at 4° C. Plates are incubated with antiserum in different dilutions for 1 hr at 37° C. followed with 1:1000 goat anti-mouse IgG-AP conjugated (Southern Biotech, Inc) for 1 hour at 37° C. Plates are developed in alkaline phosphatase substrate as described by vendor (Sigma, Inc).

Western Blot

20 μg peptide are loaded on 10% tris-glycine SDS gel (Novex, Invitrogen, Inc) after a short time of electrophoresis running, peptide is transferred onto nitrocellulose membrane (Bio-Rad, Inc). Non-specific binding to membrane is achieved by soaking membrane in blocking solution (5% non-fat milk in PBS/0.05% tween) for 1 hr at room temperature. Membranes are incubated with guinea pig anti-HRV6 or anti-HRV 14 polyclonal antibodies (ATCC) at 1:1000 in blocking solution for overnight at 4° C. After three 15 minute washes in PBS/0.05% Tween, membranes are incubated with goat anti-mouse IgG-AP conjugated antibody (Southern Biotech) in blocking solution for 1 hr at room temperature. Membrane was developed in AP substrate (Sigma SIGMA FAST™ BCIP/NBT) for 10 minutes.

Other Embodiments

All publications, patent applications, and patents mentioned in this specification are incorporated herein by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments.

Indeed, various modifications of the described modes for carrying out the invention that are obvious to those skilled in the fields of medicine, pharmacology, or related fields are intended to be within the scope of the invention. Use of singular forms herein, such as "a" and "the," does not exclude indication of the corresponding plural form, unless the context indicates to the contrary.

What is claimed is:

1. An isolated nucleic acid molecule encoding a protein comprising:
   (a) a first region comprising a rhinovirus neutralizing immunogen IV (NimIV) peptide, wherein said NimIV peptide consists of a sequence selected from the group consisting of: PVIKKR (SEQ ID NO:1), PVIKKRK (SEQ ID NO:2), PVIKKRE (SEQ ID NO:3), PVIKKRS (SEQ ID NO:4), NTEPVIKKRKGDIKSY (SEQ ID NO:10), and an 8-30 amino acid fragment of the C-terminal end of virus structural protein 1 (VP-1) of a human rhinovirus comprising one of said sequences; and
   (b) contiguous flanking sequences that do not include sequences with which the first region is contiguous in a naturally occurring virus.

2. The isolated nucleic acid molecule of claim 1, wherein the NimIV peptide is a human rhinovirus 14 (HRV14) NimIV peptide, a human rhinovirus 6 (HRV6) NimIV peptide, or a human rhinovirus 72 (HRV72) peptide.

3. A vector comprising the isolated NimIV nucleic acid molecule of claim 1.

4. The vector of claim 3, wherein the vector is a human rhinovirus vector.

5. The vector of claim 4, wherein the human rhinovirus vector is of a serotype different from that of the rhinovirus from which the sequences encoding the NimIV peptide are derived.

6. The vector of claim 5, wherein the sequences encoding the NimIV peptide are present in said human rhinovirus vector in place of NimIV sequences originally present in said vector.

7. The vector of claim 4, wherein the human rhinovirus vector is a human rhinovirus 14 (HRV14) vector.

8. The vector of claim 3, wherein the rhinovirus from which the sequences encoding the NimIV peptide are derived is human rhinovirus 6 (HRV6) or human rhinovirus 72 (HRV72).

9. The vector of claim 4, wherein the human rhinovirus vector is a human rhinovirus 14 (HRV14) vector and said rhinovirus from which the sequences encoding the NimIV peptide are derived is human rhinovirus 6 (HRV6) or human rhinovirus 72 (HRV72).

10. The vector of claim 6, wherein said vector comprises VP1 sequences and the VP1 sequences of said vector are replaced with the VP1 sequences of the rhinovirus from which the NimIV sequences are derived.

11. The vector of claim 3, wherein the vector comprises a hepatitis B core sequence to which NimIV sequences are fused.

12. A pharmaceutical composition comprising the isolated nucleic acid molecule of claim 1.

13. The pharmaceutical composition of claim 12, wherein the isolated nucleic acid molecule is comprised within a vector.

14. The pharmaceutical composition of claim 12, further comprising one or more of a pharmaceutically acceptable diluent, excipient, carrier, or adjuvant.

15. The pharmaceutical composition of claim 14, wherein the adjuvant is selected from the group consisting of a chitin microparticle and an aluminum compound.

16. The pharmaceutical composition of claim 12, further comprising sequences encoding one or more additional rhinovirus neutralizing immunogens.

17. A method of inducing an immune response to a rhinovirus in a subject, the method comprising administering to the subject an isolated NimIV nucleic acid molecule.

18. The method of claim 17, wherein the subject does not have but is at risk of developing rhinovirus infection.

19. The method of claim 17, wherein the subject has rhinovirus infection.

20. The isolated nucleic acid molecule of claim 1, wherein said NimIV peptide is 8-25, 10-20, 14-19, 15-18, or 16-17 amino acids in length.

21. The isolated nucleic acid molecule of claim 1, encoding a fusion protein comprising (a) more than one of said NimIV peptides, and/or (b) a sequence heterologous to said NimIV peptide.

22. The isolated nucleic acid molecule of claim 21, wherein said heterologous sequence is a carrier protein.

23. The isolated nucleic acid molecule of claim 21, wherein said more than one Nim IV peptides are derived from single or multiple human rhinovirus serotypes.

24. The isolated nucleic acid molecule of claim 1, wherein said NimIV peptide sequence consists of a sequence selected from the group consisting of: CKNIVPVIKKRENITTY (HRV6; SEQ ID NO:15), CNTEPVIKKRKGDIKSY (HRV14; SEQ ID NO:16), and CNPKPVIKKREGDIKTY (HRV72; SEQ ID NO:17).

* * * * *